(12) United States Patent
Buckland et al.

(10) Patent No.: US 11,622,681 B2
(45) Date of Patent: Apr. 11, 2023

(54) PROCEDURAL OPTICAL COHERENCE TOMOGRAPHY (OCT) FOR SURGERY AND RELATED METHODS

(71) Applicant: Bioptigen, Inc., Morrisville, NC (US)

(72) Inventors: Eric L. Buckland, Hickory, NC (US); Al-Hafeez Dhalla, Durham, NC (US); Robert H. Hart, Cary, NC (US)

(73) Assignee: Bioptigen, Inc., Morrisville, NC (US)

( * ) Notice: Subject to any disclaimer, the term of this patent is extended or adjusted under 35 U.S.C. 154(b) by 351 days.

(21) Appl. No.: 16/665,106

(22) Filed: Oct. 28, 2019

(65) Prior Publication Data

US 2020/0054206 A1    Feb. 20, 2020

Related U.S. Application Data

(63) Continuation of application No. 14/446,013, filed on Jul. 29, 2014, now Pat. No. 10,456,030.

(Continued)

(51) Int. Cl.
| | |
|---|---|
| *A61B 3/00* | (2006.01) |
| *A61B 3/10* | (2006.01) |
| *A61B 3/107* | (2006.01) |
| *A61B 3/103* | (2006.01) |
| *A61F 2/16* | (2006.01) |

(Continued)

(52) U.S. Cl.
CPC ............ *A61B 3/102* (2013.01); *A61B 3/0025* (2013.01); *A61B 3/0041* (2013.01); *A61B 3/103* (2013.01); *A61B 3/1005* (2013.01); *A61B 3/107* (2013.01); *A61F 2/16* (2013.01); *A61B 2034/108* (2016.02);

(Continued)

(58) Field of Classification Search
CPC ....................................................... A61B 3/102
See application file for complete search history.

(56) References Cited

U.S. PATENT DOCUMENTS

| | | | |
|---|---|---|---|
| 4,167,302 A | 9/1979 | Karasawa | |
| 4,431,258 A | 2/1984 | Fye | |

(Continued)

FOREIGN PATENT DOCUMENTS

| | | |
|---|---|---|
| CN | 101382644 A | 3/2009 |
| CN | 102612342 A | 7/2012 |

(Continued)

OTHER PUBLICATIONS

Brandenburg R. et al., "Real-time in vivo imaging of dental tissue by means of optical coherence tomography (OCT)", *Optics Communications*, 227 (2003), 203-211.

(Continued)

*Primary Examiner* — Joseph M Santos Rodriguez
(74) *Attorney, Agent, or Firm* — Stanek Lemon Crouse & Meeks, P.A.

(57) ABSTRACT

Methods are provided for performing a surgical procedure using optical coherence tomography (OCT) including extracting lenticular material from within a capsular bag of the eye of a patient; placing a replacement lens within the capsular bag after extraction of the lenticular material from the capsular bag; acquiring a plurality of OCT images that visualize the placement of the replacement lens within the capsular bag; and determining from the plurality of OCT images a degree of contact of the posterior surface of the replacement lens with the posterior portion of the capsular bag.

17 Claims, 21 Drawing Sheets

Related U.S. Application Data

(60) Provisional application No. 61/984,062, filed on Apr. 25, 2014, provisional application No. 61/914,099, filed on Dec. 10, 2013, provisional application No. 61/859,465, filed on Jul. 29, 2013.

(51) Int. Cl.
  *A61F 9/008* (2006.01)
  *A61B 90/00* (2016.01)
  *A61B 34/10* (2016.01)

(52) U.S. Cl.
  CPC .......... *A61B 2090/3735* (2016.02); *A61F 2009/00851* (2013.01)

(56) References Cited

U.S. PATENT DOCUMENTS

| | | |
|---|---|---|
| 4,544,243 A | 10/1985 | Munnerlyn |
| 4,561,080 A | 12/1985 | Yamazaki |
| 4,930,868 A | 6/1990 | Gerlitz |
| 5,055,663 A | 10/1991 | Morimoto et al. |
| 5,061,018 A | 10/1991 | Pederson et al. |
| 5,103,439 A | 4/1992 | Bierhoff et al. |
| 5,168,386 A | 12/1992 | Galbraith |
| 5,220,450 A | 6/1993 | Iizuka |
| 5,491,524 A | 2/1996 | Hellmuth et al. |
| 5,493,109 A | 2/1996 | Wei et al. |
| 5,795,295 A | 8/1998 | Hellmuth et al. |
| 5,889,750 A | 3/1999 | Summers et al. |
| 5,907,431 A | 5/1999 | Stuttler |
| 6,004,314 A | 12/1999 | Wei et al. |
| 6,333,781 B1 | 12/2001 | Shigematsu ......... G02B 13/143 355/53 |
| 6,419,360 B1 | 7/2002 | Hauger et al. |
| 6,426,840 B1 | 7/2002 | Partanen et al. |
| 6,451,010 B1 | 9/2002 | Angeley |
| 6,678,090 B2 | 1/2004 | Spink |
| 6,763,259 B1 | 7/2004 | Hauger et al. |
| 6,943,942 B2 | 9/2005 | Horiguchi et al. |
| 7,072,047 B2 | 7/2006 | Westphal et al. |
| 7,145,727 B2 | 12/2006 | Hsieh |
| 7,246,905 B2 | 7/2007 | Benedikt |
| 7,387,385 B2 | 6/2008 | Sander |
| 7,408,705 B2 | 8/2008 | Horiguchi et al. |
| 7,481,536 B2 | 1/2009 | Wong |
| 7,669,262 B2 | 3/2010 | Skripps et al. |
| 7,699,468 B2 | 4/2010 | Gaida |
| 7,719,692 B2 | 5/2010 | Izatt et al. |
| 7,733,497 B2 | 6/2010 | Yun et al. |
| 7,742,174 B2 | 6/2010 | Izatt et al. |
| 7,791,794 B2 | 9/2010 | Reimer et al. |
| 7,839,494 B2 | 11/2010 | Reimer et al. |
| 7,889,423 B2 | 2/2011 | Reimer et al. |
| 7,901,080 B2 | 3/2011 | Hauger et al. |
| 8,023,120 B2 | 9/2011 | Reimer et al. |
| 8,049,873 B2 | 11/2011 | Hauger et al. |
| 8,189,192 B2 | 5/2012 | Huening et al. |
| 8,310,674 B2 | 11/2012 | Huening et al. |
| 8,348,427 B2 | 1/2013 | Buckland et al. |
| 8,401,257 B2 | 3/2013 | Izatt et al. |
| 8,425,037 B2 | 4/2013 | Uhlhorn et al. |
| 8,625,104 B2 | 1/2014 | Izatt et al. |
| 8,693,745 B2 | 4/2014 | Izatt et al. |
| 8,777,412 B2 | 7/2014 | Buckland et al. |
| 8,797,530 B2 | 8/2014 | Saxer et al. |
| 8,820,931 B2 | 9/2014 | Walsh |
| 8,864,309 B2 | 10/2014 | Buckland |
| 2002/0173778 A1 | 11/2002 | Knopp et al. |
| 2003/0139736 A1 | 7/2003 | Sander |
| 2003/0218755 A1 | 11/2003 | Wei et al. |
| 2004/0036838 A1 | 2/2004 | Podoleanu et al. |
| 2004/0109231 A1 | 6/2004 | Haisch et al. |
| 2005/0068881 A1 | 3/2005 | Kimura et al. |
| 2005/0277913 A1 | 12/2005 | McCary |
| 2005/0283058 A1 | 12/2005 | Choo-Smith et al. |
| 2006/0050408 A1 | 3/2006 | Hakko et al. |
| 2006/0195074 A1 | 8/2006 | Bartoli |
| 2007/0030446 A1 | 2/2007 | Su et al. |
| 2007/0159595 A1 | 7/2007 | Fukuma et al. |
| 2007/0258095 A1 | 11/2007 | Olivier et al. |
| 2007/0282313 A1 | 12/2007 | Huang et al. |
| 2007/0291277 A1 | 12/2007 | Everett et al. |
| 2008/0004610 A1 | 1/2008 | Miller et al. |
| 2008/0117504 A1 | 5/2008 | Reimer et al. |
| 2008/0133019 A1 | 6/2008 | Andrysek |
| 2008/0198329 A1 | 8/2008 | Gaida |
| 2008/0304144 A1 | 12/2008 | Reimer et al. |
| 2009/0141240 A1 | 6/2009 | Weitz et al. |
| 2009/0244485 A1 | 10/2009 | Walsh et al. |
| 2009/0257065 A1 | 10/2009 | Hauger et al. |
| 2010/0030056 A1 | 2/2010 | Abramov .............. A61B 3/165 600/401 |
| 2010/0309478 A1 | 12/2010 | Reimer et al. |
| 2010/0324542 A1 | 12/2010 | Kurtz |
| 2010/0324543 A1 | 12/2010 | Kurtz |
| 2011/0001926 A1 | 1/2011 | Mann et al. |
| 2011/0028948 A1 | 2/2011 | Raksi et al. |
| 2011/0096291 A1 | 4/2011 | Buckland et al. |
| 2011/0173778 A1 | 7/2011 | Wales |
| 2011/0202046 A1 | 8/2011 | Angeley |
| 2011/0242483 A1 | 10/2011 | Shea et al. |
| 2011/0299034 A1 | 12/2011 | Walsh |
| 2012/0022408 A1* | 1/2012 | Hubschman ........... A61B 90/36 606/1 |
| 2012/0026462 A1 | 2/2012 | Uhlhorn |
| 2012/0063660 A1 | 3/2012 | Imamura .............. A61B 5/0066 382/131 |
| 2012/0074294 A1 | 3/2012 | Streuber et al. |
| 2012/0184846 A1 | 7/2012 | Izatt et al. |
| 2012/0197102 A1 | 8/2012 | Hanebuchi |
| 2012/0215155 A1 | 8/2012 | Muller et al. |
| 2012/0242988 A1 | 9/2012 | Saxer et al. |
| 2012/0262720 A1 | 10/2012 | Brown et al. |
| 2012/0316545 A1 | 12/2012 | Blumenkranz et al. |
| 2013/0141695 A1 | 6/2013 | Buckland et al. |
| 2013/0158531 A1 | 6/2013 | Goldshleger |
| 2013/0165763 A1 | 6/2013 | Huang ................. A61B 3/16 600/401 |
| 2013/0172861 A1 | 7/2013 | Youssefi |
| 2013/0190737 A1 | 7/2013 | Muller et al. |
| 2013/0265545 A1 | 10/2013 | Buckland et al. |
| 2014/0194860 A1 | 7/2014 | Dick |

FOREIGN PATENT DOCUMENTS

| | | | |
|---|---|---|---|
| CN | 102696125 A | 7/2012 | |
| EP | 0 697 611 A2 | 2/1996 | |
| EP | 1 659 438 B1 | 3/2009 | |
| EP | 2 322 083 A1 | 5/2011 | |
| JP | 2011-024842 A | 2/2011 | |
| JP | 2011-104370 A | 6/2011 | |
| JP | 2011-147612 A | 8/2011 | |
| WO | WO 2008/034609 A1 | 3/2008 | |
| WO | WO 2011/017019 A2 | 2/2011 | |
| WO | WO 2011/060356 A1 | 5/2011 | |
| WO | WO 2011/091326 A1 | 7/2011 | |
| WO | WO 2013017513 A2 | 2/2013 | ......... A61F 9/00825 |
| WO | WO 2013/059719 A1 | 4/2013 | |
| WO | WO 2013/151879 A1 | 10/2013 | |

OTHER PUBLICATIONS

Davis A.M. et al., "In vivo spectral domain optical coherence tomography volumetric imaging and spectral Doppler velocimetry of early stage embryonic chicken heart development", *J. Opt. Soc. Am. A.*, vol. 25, No. 12, Dec. 2008, pp. 3134-3143.

Geerling G. et al., "Intraoperative 2-Dimensional Optical Coherence Tomography as a New Tool for Anterior Segment Surgery", *Arch Ophthalmol.* 2005;123:253-257.

Izatt J.A. et al., "Optical coherence microscopy in scattering media", *Optics Letters*, vol. 19, No. 8, Apr. 15, 1994, pp. 590-592.

(56) References Cited

OTHER PUBLICATIONS

Izatt S. D. et al., "In Vivo imaging of the *Drosophila melanogaster* heart Using a Novel Optical Coherence Tomography Microscope", *Proc. Of SPIE*, vol. 5701, pp. 122-127, Downloaded from SPIE Digital Library on May 16, 2011.
Maschio M.D. et al., "Three-dimensional in vivo scanning microscopy with inertia-free focus control", *Optics Letters*, Sep. 1, 2011, vol. 36, No. 17, pp. 3503-3505.
Murall, Supraja "*Design Of A Dynamic Focusing Microscope Objective for OCT Imaging*", MS Thesis, University of Central Florida, Orlando, Florida, 2005.
Notification of Transmittal of the International Search Report and the Written Opinion of the International Searching Authority, or the Declaration, PCT/US2013/034544, dated Jul. 3, 2013.
Notification of Transmittal of the International Search Report and the Written Opinion of the International Searching Authority, of the Declaration, PCT/US2012/067951, dated Mar. 5, 2013.
Qi B. et al., "Dynamic focus control in high-speed optical coherence tomography based on a microelectromechanical mirror", *Optics Communications*, 232 (2004), 123-128.
Radhaknshnan S. et al., "Real-Time Optical Coherence Tomography of the Anterior Segment at 1310 nm", *Arch Ophthalmol.*, 2001;119:1179-1185.
Tao Y.K. et al., "Intraoperative spectral domain optical coherence tomography for vitreoretinal surgery", *Optics Letters*, Oct. 15, 2010, vol. 35, No. 20, pp. 3315-3317.
Invitation to Pay Additional Fees and, Where Applicable, Protest Fees, PCT/US2014/048552, Oct. 31, 2014.
Notification Concerning Transmittal of International Preliminary Report on Patentability, PCT/US2013/034544, dated Oct. 16, 2014.
Notification of Transmittal of the International Search Report and the Written Opinion of the International Searching Authority, or the Declaration, PCT/US2014/048552, dated Feb. 2, 2015, 15 pages.
Notification of Transmittal of the International Search Report and the Written Opinion of the International Searching Authority, or the Declaration, PCT/US2014/040836, dated Feb. 4, 2015, 15 pages.
Notification Concerning Transmittal of International Preliminary Report on Patentability, PCT/US2014/040836, dated Dec. 17, 2015.
Notification Concerning Transmittal of International Preliminary Report on Patentability, PCT/US2014/048552, dated Feb. 11, 2016.
Dal Maschio et al. "Three-dimensional in vivo scanning microscopy with inertia-free focus control," Optics Letters, vol. 36, No. 17, Sep. 1, 2011, pp. 3503-3505.
First Office Action, Chinese Patent Application No. 201380029541.0, dated Feb. 22, 2016, 15 pages.
International Search Report and Written Opinion Corresponding to International Application No. PCT/US2014/053113; dated Dec. 2, 2014, 11 Pages.
Notification Concerning Transmittal of International Preliminary Report on Patentability, PCT/US2014/053113, dated Mar. 10, 2016.
Notification Concerning Transmittal of International Preliminary Report on Patentability, PCT/US2014/040836, dated Dec. 17, 2015, 10 pages.
First Notification of Office Action, Chinese Patent Application No. 201480040460.5, dated Oct. 10, 2016, 14 pages.
Notification of Reasons for Refusal, Japanese Patent Application No. 2016-525842, dated Jan. 10, 2017, 11 pages.
Second Notification of Office Action, Chinese Patent Application No. 201480032285.5, dated Jul. 25, 2017, 15 pages.
Communication pursuant to Article 94(3) EPC, European Application No. 14 752 503.4, dated Oct. 4, 2017, 7 pages.
Decision of Refusal, JP 2016-525842, dated Jan. 9, 2018, 14 pages.

* cited by examiner

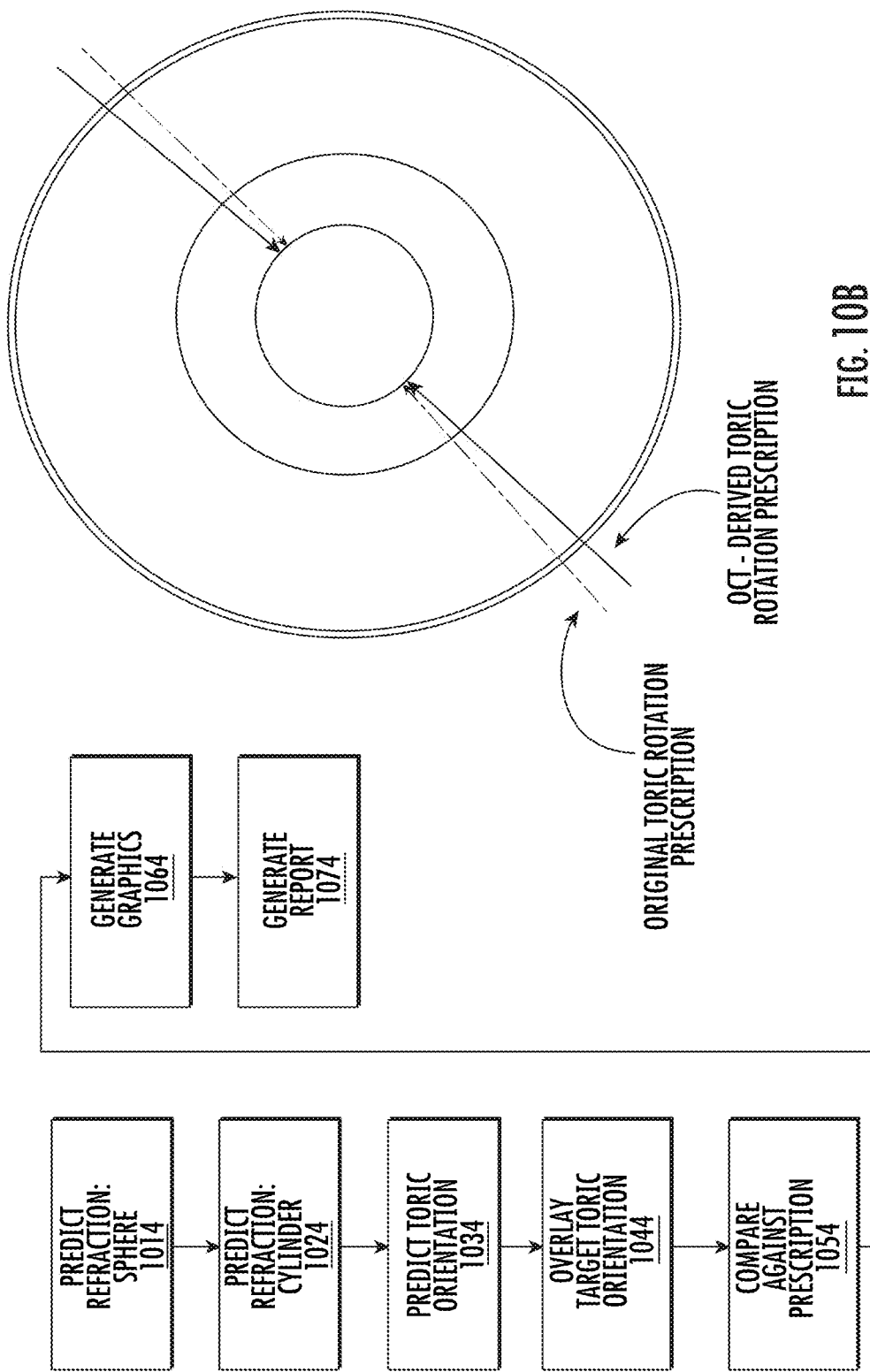

PROCEDURAL OPTICAL COHERENCE TOMOGRAPHY (OCT) FOR SURGERY AND RELATED METHODS

CLAIM OF PRIORITY

The present application is a continuation of U.S. patent application Ser. No. 14/446,013, filed Jul. 29, 2014, which claims priority to U.S. Provisional Application No. 61/859,465, filed Jul. 29, 2013; U.S. Provisional Application No. 61/914,099, filed Dec. 10, 2013; and U.S. Provisional Application No. 61/984,062, filed Apr. 25, 2014, the disclosures of which are hereby incorporated herein by reference as if set forth in their entirety.

STATEMENT OF GOVERNMENT SUPPORT

This inventive concept was funded in-part with government support under Grant Application ID R44EY018021-03 by the National Institutes of Health, National Eye Institute. The United States Government has certain rights in this inventive concept.

FIELD

The present inventive concept relates generally to image-guided surgery, image-guided ophthalmic surgery, image-guided cataract and cornea surgery, and more particularly, to image-guided surgery using optical coherence tomography (OCT).

BACKGROUND

Surgical microscopes provide a magnified view of the operating field to the surgeon. Ophthalmic surgical microscopes are commonly stereo zoom microscopes with binocular view ports for the surgeon, and frequently have one or two observer view ports at ninety degrees (left and right) to the surgeon. The working distance between the objective lens of the microscope and the surface of a patient eye may range from about 100 mm to about 200 mm in order to allow the surgeon sufficient working area.

Surgical microscopes are tailored to provide clear optical view to the subject, with uniform illumination and accurate color temperature. Stereo microscopes provide a degree of parallax to provide the surgeon with a sense of space and topography. Occasionally dyes are used to emphasize topography. High definition video is being offered into surgical microscopes to improve visual clarity. Topographic 3D video technologies adopted from entertainment industry, such as polarization-diversity stereoscopy, are now being added to increase the sense of depth.

Such surgical stereo microscopes are constrained to surface visualization. Optical coherence tomography (OCT) is now a well-established technology for imaging beneath an optically translucent surface. High resolution OCT offers a capability to observe sub-surface structures, complementary to the surface views of stereo, high definition and 3D surgical microscopes. Optical coherence tomography is a standard of care in retinal diagnostics, and is finding some use in cornea imaging and metrology OCT is only beginning to find use in intra-surgical imaging. Bioptigen offers a handheld ophthalmic OCT system has been FDA cleared for imaging patients under anesthesia. This device is finding application in handheld and mounted configurations for structural imaging during ophthalmic surgeries, including retinal surgery and cornea transplant surgery and an adjunct to surgeon's microscope visualization.

OCT is now incorporated in certain ophthalmic surgical laser systems. OCT is incorporated in LensX and Optimedica femtosecond laser assisted cataract (FLAC) surgical systems to provide ranging to the crystalline lens as a guidance device to facilitate focus of the surgical laser. At present, this ranging function is the limit of the application of the OCT to the surgical procedure.

SUMMARY

Some embodiments of the present inventive concept provide methods for performing a surgical procedure using optical coherence tomography (OCT). The method includes orienting the subject for the surgical procedure, wherein orienting comprises imaging a region of the subject that contains a structure having a known orientational asymmetry, testing the image for the presence and location of the structure, and confirming correct orientation of the subject using the OCT image of the structure having the known orientational asymmetry; obtaining at least one image of the surgical region of the subject using OCT and constructing an initial structural view of the surgical region; computing at least one clinical parameter relevant as an end point for assessing the outcome of the surgical procedure using data derived from the OCT image; periodically assessing a surgical process and monitoring clinical outcomes related to the surgical procedure using changes to the OCT-derived structural view of the surgical region OCT or the changes to the computed clinical parameters derived from the at least an OCT image; determining if a surgical plan for the surgical procedure needs modification based on the periodic assessment and/or monitoring; modifying the surgical plan for the surgical procedure if it is determined modification is needed; and repeatedly assessing and monitoring, determining and modifying until it is determined that modification is not needed.

In further embodiments of the present inventive concept, before concluding the surgical procedure on the subject, final clinical outcomes of the surgical procedure may be assessed by testing computed clinical parameters derived from the at least one OCT image against a target value.

In still further embodiments of the present inventive concept determining that modification of a surgical plan is not needed may be followed by acquiring at least one OCT image of a surgical wound and assessing wound integrity of a surgical site related to the surgical procedure.

In some embodiments of the present inventive concept, assessing wound integrity may be followed by concluding the surgical procedure if the assessment of the final clinical outcomes and the wound integrity are satisfactory. A report for the surgical procedure may be generated including at least one computed clinical parameter derived from at least one OCT image.

In further embodiments, the computed clinical parameters for the surgical procedure may include a cornea thickness, a cornea curvature, a lens thickness, a lens curvature, a cornea refractive power, a lens refractive power, an iridocorneal angle, a sclear thickness, a conjunctival thickness, a direction of an optical axis, an orientation of a refractive astigmatism, a thickness of a an edema, a length of a tissue membrane or tear, a width of a surgical incision, a map or a count of surgical debris within a surgical field, a map or measure of degree of contact between an implanted device and surrounding tissue, and orientation of an implanted device relative to a neighboring structure or an optical or physical axis. The parameters may be computed from measurements derived from the at least one OCT image.

In still further embodiments, the surgical procedure is related to an eye of the subject; the surgical procedure may be cataract surgery or cornea surgery; the surgical procedure may be a retinal surgery, or the surgical procedure may be a glaucoma surgery.

In some embodiments, orienting the subject for the procedure may include obtaining a wide angle view of a portion of the eye of the subject using OCT for use in orienting the eye; identifying an orientationally asymmetric physiological structure visible within the at least one OCT image that confirms the eye under test to be either the right eye or the left eye; creating graphical display representative of the imaged portion of the eye of the subject using data derived from the at least one OCT image; and displaying the graphical display to a surgeon performing the surgical procedure, wherein the graphical display includes at least a graphical element that orients the surgeon performing the surgical procedure to the orientation of the eye.

In further embodiments, obtaining the structural view of the eye includes creating a structural map of the subject, wherein creating the structural map comprises: acquiring a plurality of OCT images across the eye of the subject; applying segmentation algorithms to the acquired OCT images to differentiate boundaries of structures of the eye identified in the plurality of OCT images; and computing clinical parameters associated with structure of the eye.

In still further embodiments, computing clinical parameters may include includes one or more of computing keratometric values of a cornea, a lens or the combination of a cornea and a lens; and computing an abberometry map of a cornea, a lens or the combination of a cornea and a lens.

In some embodiments, the method may further include providing a set of graphics based on the keratometric assessment of the eye for use by a surgeon performing the surgical procedure, the set of graphics including at least one of three dimensional images, wire-frame models and en face projections aligned to the surgeon's view of the eye.

In further embodiments, obtaining a structural map of the subject may be followed by: predicting, based on OCT data, refraction including sphere, cylinder and toric orientation to provide an OCT-computed prescription; displaying the OCT-computed prescription on graphical display to a surgeon performing the surgical procedure; and comparing an original prescription to the OCT-computed prescription; and displaying result of comparison on the graphical display to the surgeon allowing the surgeon to access a final prescription based on the comparison.

In still further embodiments, performing a capsulotomy using OCT may include acquiring an OCT image of a lens of the eye; displaying a target size, shape and position and a current shape of the capsulotomy on a graphical display derived from the acquire OCT image; and displaying an error function on the graphical display based on the target and the current shape of the capsulotomy to provide guidance to a surgeon performing the surgical procedure.

In some embodiments, an audible alert may be provided when the error function exceeds a pre-determined threshold.

In further embodiments, the method may further include performing phaco fragmentation, wherein phaco fragmentation includes acquiring a plurality of OCT images of the eye intermittently or continuously allowing a surgeon performing the surgical procedure to evaluate risks and abnormalities during the procedure.

In still further embodiments, the method may include identifying epithelial cells, wherein identifying epithelial cells includes obtaining a high density OCT scan of a posterior capsule of the eye; segmenting the high density image to identify an anterior surface of the posterior capsule; identifying residual epithelial cells or debris as a function of distance off a capsular bag; and displaying the presence of the residual cells to a surgeon performing the surgical procedure.

In some embodiments, the method further includes orienting the inter-ocular lens (IOL) using OCT to guide the orientation.

In further embodiments, the method further includes managing Intraocular pressure (IOP) using OCT, whereby managing intraocular pressure comprises comparing a pre-surgical shape of a cornea to an intrasurgical or post-surgical shape of a cornea.

Still further embodiments provided a system for performing a surgical procedure using optical coherence tomography (OCT). The system comprises a processor; and a memory coupled to the processor and comprising computer readable program code that when executed by the processor causes the processor to perform operations comprising: orienting the subject for the surgical procedure, wherein orienting comprises imaging a region of the subject that contains a structure having a known orientational asymmetry, testing the image for the presence and location of the structure, and confirming correct orientation of the subject using the OCT image of the structure having the known orientational asymmetry; obtaining at least one image of the surgical region of the subject using OCT and constructing an initial structural view of the surgical region; computing at least one clinical parameter relevant as an end point for assessing the outcome of the surgical procedure using data derived from the OCT image; periodically assessing a surgical process and monitoring clinical outcomes related to the surgical procedure using changes to the OCT-derived structural view of the surgical region OCT or the changes to the computed clinical parameters derived from the at least an OCT image; determining if a surgical plan for the surgical procedure needs modification based on the periodic assessment and/or monitoring; modifying the surgical plan for the surgical procedure if it is determined modification is needed; and repeatedly assessing and monitoring, determining and modifying until it is determined that modification is not needed.

Some embodiments of the present inventive concept provide a computer program product for performing a surgical procedure using optical coherence tomography (OCT). The computer program product including a non-transitory computer readable storage medium having computer readable program code embodied in the medium, the computer readable program code comprising: computer readable program code configured to orient the subject for the surgical procedure, wherein the computer readable program code configured to orient comprises computer readable program code to image a region of the subject that contains a structure having a known orientational asymmetry, test the image for the presence and location of the structure, and confirm correct orientation of the subject using the OCT image of the structure having the known orientational asymmetry; computer readable program code configured to obtain at least one image of the surgical region of the subject using OCT and constructing an initial structural view of the surgical region; computer readable program code configured to compute at least one clinical parameter relevant as an end point for assessing the outcome of the surgical procedure using data derived from the OCT image; computer readable program code configured to periodically assess a surgical process and monitoring clinical outcomes related to the surgical procedure using changes to the OCT-derived structural view of the surgical region OCT or the changes to the computed clinical parameters derived from the at least an OCT image; computer readable program code configured to determine if a surgical plan for the surgical procedure needs modification based on the periodic assessment and/or monitoring; computer readable program code configured to modify the surgical plan for the surgical procedure if it is determined modification is needed; and computer readable program code configured to repeatedly assess and monitor, determine and modify until it is determined that modification is not needed.

Further embodiments of the present inventive concept provide methods for performing a surgical procedure using optical coherence tomography (OCT), the method comprising extracting lenticular material from within a capsular bag of the eye of a patient; acquiring at least one OCT image of an interior region of the capsular bag after extraction of the majority of lenticular material from within the capsular bag; determining from the at least one OCT image the presence of cellular debris remaining within the interior of the capsular bag; and extracting at least a portion of the remaining cellular debris from the interior of the capsular bag.

In still further embodiments of the present inventive concept, determining the presence of cellular debris may include displaying location of cellular debris within the surgical field of view on a graphical display.

In some embodiments, extracting at least a portion of the cellular debris may be followed by acquiring at least one additional OCT image; and determining from the at least an additional OCT image the residual presence of cellular debris.

Further embodiments of the present inventive concept provide methods for performing a surgical procedure using optical coherence tomography (OCT), the method comprising: extracting lenticular material from within a capsular bag of the eye of a patient; placing a replacement lens within the capsular bag after extraction of the lenticular material from the capsular bag; acquiring a plurality of OCT images that visualize the placement of the replacement lens within the capsular bag; and determining from the plurality of OCT images a degree of contact of the posterior surface of the replacement lens with the posterior portion of the capsular bag.

In still further embodiments, determining the degree of contact of the posterior surface of the replacement lens with the posterior portion of the capsular bag may include use of a graphical display indicating a circumferential boundary of contact of the posterior surface of the replacement lens with the posterior capsular bag.

In some embodiments of the present inventive concept, determining the degree of contact of the replacement lens with the capsular bag may be followed by performing a surgical procedure to adjust the placement of the replacement lens within the capsular bag.

Further embodiments of the present inventive concept provide methods for prescribing inter-ocular lens (IOL) using optical coherence tomography (OCT), the method comprising computing target refraction from acquired OCT data, refraction including at least one of sphere, cylinder and toric orientation; displaying the OCT computed target refraction and orientation on a graphical display for a surgeon performing a surgical procedure; comparing the computed prescription to an original prescription on the graphical display; and determining a final prescription based on information presented on the graphical display.

In still further embodiments, the graphical display may include an en face surgeon compass view.

In some embodiments, a report of the surgical procedure may be generated.

BRIEF DESCRIPTION OF THE DRAWINGS

FIGS. 10A and 10B are a flow chart and a diagram, respectively, illustrating operations in prescribing inter-ocular lens (IOL) in accordance with embodiments of the present inventive concept.

DETAILED DESCRIPTION

Figure 1A:
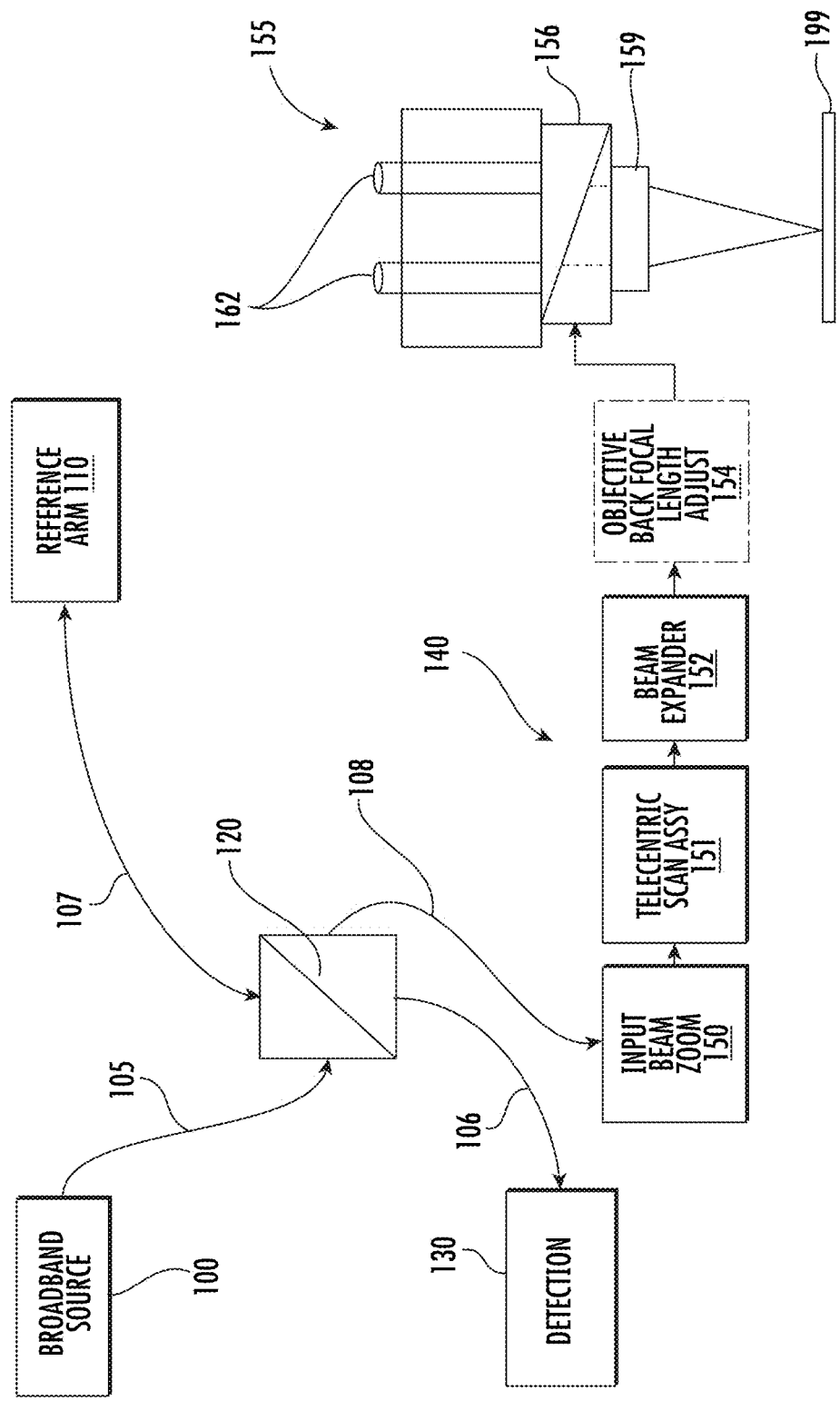
FIG. 1A is a block diagram of a surgical microscope that may be used in accordance with some embodiments of the present inventive concept.

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

Aspects of the present disclosure are described herein with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks. As used herein, "a processor" may refer to one or more processors.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

Although many of the examples discussed herein refer to the sample/subject being an eye, specifically, the retina, cornea, anterior segment and lens of the eye, embodiments of the present inventive concept are not limited to this type of sample. Any type of sample that may be used in conjunction with embodiments discussed herein may be used without departing from the scope of the present inventive concept.

As discussed above, ophthalmic surgical microscopes can provide surgeons a magnified view of various areas of the eye on which they are operating. However, there are many ophthalmic surgical procedures that may benefit from the three-dimensional high-resolution tomographic imaging provided by Optical Coherence Tomography (OCT). Thus, integrating an OCT system into a surgical microscope may provide greater capabilities and enable procedures that currently cannot be performed with only conventional stereoscopic imaging. Conventional surgical microscopes incorporating OCT generally provide static imaging incapable of adapting for the region of interest in the sample. Taking the example of an eye, conventional systems cannot typically adapt to the difference imaging requirements for imaging the corneal region, the anterior chamber and crystalline lens, and the structures on the retina. Ophthalmic surgery requires precise visualization targeted to the specific requirements of specific surgical procedures. Procedural OCT can be used to improve outcomes, reduce risks, and reduce costs for the patient, the healthcare provider, and the insurer.

An ideal OCT surgical microscope system would be adaptable to tailor the imaging characteristics for the various regions of interest. An ideal OCT surgical microscope would have the following set of attributes: true telecentric scanning for accurate representation of subject topography; variable numerical aperture to control the distribution of illumination over a depth of field and to allow control of lateral resolution at the position of focus; variable focus to allow independent control of the OCT focal position relative to the ocular focus of the visual microscope; a wide field of view (FOV) wherein the scanning optical path length is held maximally constant, both to keep physiopathology within the OCT depth of field and to avoid visual distortions of the scanned field; and adjustability to accommodate a wide range of microscope main objectives, to provide versatility to the surgeon for various surgical procedures. It is further desirable to reduce any alterations to the physical working distances of the microscope to which the surgeon may be accustomed. These distances include the distance between the main objective and the subject, and the distance between the microscope oculars and the subject. Specific systems that address these requirements are discussed in, for example, U.S. patent application Ser. No. 13/836,576 entitled Surgical Microscopes Using Optical Coherence Tomography and Related Systems and Methods, the disclosure of which is incorporated herein by reference as if set forth in its entirety.

The most common ophthalmic surgical procedure is cataract surgery, wherein an opacified crystalline lens that has become sufficiently opaque to cause vision loss is removed from the capsular bag that is the sack-like structure that surrounds, shapes and holds the lens and connects the lens to the musculature of the eye, and a replacement polymer intraocular lens is placed in its stead. Approximately 22 million cataract surgeries are performed annually. Cataract surgeries are moderately invasive, with generally high success rate and low risk. Most elements of risk are readily treated in outpatient follow up visits to correct residual refractive error (prescribing glasses) and clearing post-surgical opacifications originating from the growth of residual cellular material. While these follow-ups are manageable, they contribute to reduced patient satisfaction and increased economic costs.

More serious risks are associated with rarer outcomes, including endophthalmitis, retinal edema, and retinal tears and detachments. Endophthalmitis, while present in less than 1% of cases, is associated with bacteria on the surface of the eye and poor wound healing. Endophthalmitis can have disastrous vision outcomes for the patient. Damage to the retina is associated with tears in the capsular bag, and stress to the zonules that couple the capsular bag to the peripheral retina and are associated with accommodation. Retinal detachments may occur following 2% of procedures, and may not occur for weeks or months following surgery.

Though adverse events may be frequent but manageable, or serious but rare, in a procedure that impacts 20 million people or more annually it is desirable to improve outcomes and reduce risks to the extent possible and practicable. Intra-surgical procedural OCT properly deployed, as described herein, can improve the accuracy of surgical procedures, providing improved sub-surface visualization, in situ metrology and diagnostics, and a structural and wound integrity assessment to improve surgical outcomes and reduce risks for the patient, the healthcare provider, and the insurer.

The Intra-surgical procedural OCT systems and methods are discussed herein with respect to cataract surgery; however, embodiments of the present inventive concept are not limited thereto. The systems and methods discussed herein are applicable to other ophthalmic procedures, including cornea transplant surgeries and retinal repair surgeries without departing from the scope of the present inventive concept. In some embodiments, details of the imaging system may be modified to image particular structures, or the methods may be tailored to the particular surgical plan. The concept of intra-surgical procedural OCT may extend as well to other surgeries, therapies, and laboratory procedures to accomplish specific objectives, where qualitative and quantitative feedback from a depth resolved imaging system are desired to improve outcomes.

Some embodiments of the present inventive concept enable a telecentric scanning system over a wide field of view (FOV). As used herein, "telecentric" refers to maintaining constant pointing of the scanning beam parallel to the optical axis across the field of view. In these embodiments, the system images to a field flatness of better than 1% over the field of view and the telecentricity of the scanning optics ensure dimensional accuracy of visualization.

Some embodiments of the present inventive concept provide for independent control of a focal position and magnification of the scanning OCT beam, wherein the focus and magnification may be controlled independently.

Some embodiments of the present inventive concept provide for imaging in multiple regions during the course of a procedure in order to provide feedback and guidance to a surgeon or surgical system during the surgical procedure.

Some embodiments of the present inventive concept provide for multiple views of the OCT-derived image data in order to provide the surgeon with a perspective consistent with their direct and microscope-enable view.

Some embodiments of the present inventive concept identify landmarks from the OCT-derived image data that provide instruction on the orientation of the subject, such that relative orientation or changes in orientation may be monitored during the course of the procedure.

Some embodiments of the present inventive concept provide for a multi-dimensional map of the optically accessible structures of the subject, and in particular to provide a three-dimensional map of the structure across an extended range.

In some embodiments of the present inventive concept, the multi-dimensional map may be constructed of multiple images that are acquired, corrected for optical beam refraction, and accurately mosaiced, such as to create a dimensionally accurate three-dimensional model of the anatomy made available to the surgeon for visualization and metrology.

Some embodiments of the present inventive concept provide for clinically relevant computations derived from the OCT-derived images and three-dimensional models of the anatomy, and that the clinically relevant information be displayed so as to provide actionable information to guide the surgeon during the procedure.

Some embodiments of the present inventive concept of the clinically derived data may include the provision of a prescription for a device, such as an inter-ocular lens (IOL), or for a surgical cutting or shaping procedure. This prescription may be used to test and confirm an initial prescription provided prior to the surgical procedure, may be used to modify the prescription as a result of an intentional or unintentional occurrence during the procedure, or may be the sole prescription used to guide a decision within the procedure.

Some embodiments of the present inventive concept provide guidance to modify the procedure to change an anatomy or a characteristic of an anatomy, particularly to control a clinical outcome, and particularly a clinical outcome that may be measurable using one or more of the clinically relevant data.

Embodiments of the present inventive concept may be used during cataract surgery to measure a shape associated with a cornea prior to surgery, remeasure the shape at a relevant point during the surgery, compute a difference in shape, and use the difference in shape to provide guidance to a change of pressure within the eye. The surgeon may then use this information to increase or decrease a pressure within the eye to control a clinically relevant outcome of the procedure.

Some embodiments of the present inventive concept may be used during cataract surgery is to obtain a measure of an optical aberration associated with the optical elements within the visual path of the eye, assess a corrective pathway associated with modifying a stress in the cornea of the eye, and provide guidance to the surgeon to create or relieve a stress in the cornea to achieve a desired change in an aberration. The same procedure might be used to verify the efficacy of the procedure to modify the stress of the cornea.

Example systems for use in accordance with some embodiments of the present inventive concept will now be discussed with respect to FIGS. 1A and 1B. It will be understood that these systems are provided for example purposes only and, thus, embodiments of the present inventive concept should not be limited thereto. Referring first to FIG. 1A, a block diagram of an OCT surgical microscope in accordance with some embodiments of the present inventive concept will be discussed. As illustrated in FIG. 1A, the system includes a broadband source 100, a reference arm 110 and a sample arm 140 coupled to each other by a beamsplitter 120. The beamsplitter 120 may be, for example, a fiber optic coupler or a bulk or micro-optic coupler. The beamsplitter 120 may provide from about a 50/50 to about a 90/10 split ratio. As further illustrated in FIG. 1A, the beamsplitter 120 is also coupled to a wavelength or frequency sampled detection module 130 over a detection path 106 that may be provided by an optical fiber.

As further illustrated in FIG. 1A, the source 100 is coupled to the beamsplitter 120 by a source path 105. The source 100 may be, for example, a superluminescent light emitting diode (SLED) or wavelength-tunable source. The reference arm 110 is coupled to the beamsplitter 120 over a reference arm path 107. Similarly, the sample arm 140 is coupled to the beamsplitter 120 over the sample arm path 108. The source path 105, the reference arm path 107 and the sample arm path 108 may all be provided by optical fiber. Alternative implementations of optical coherence tomography imaging systems, including time domain swept source, and angle-resolved implementations are known in the art and the procedures in this invention are not limited to a particular optical coherence tomography architecture.

As further illustrated in FIG. 1A, the surgical microscope 155 includes two oculars (binocular view ports) 162 for the surgeon to view the sample 199. The surgical microscope 155 of FIG. 1A includes a modified dichroic filter 156 and an optimized objective lens 159 in accordance with embodiments discussed herein. The objective lens 159 is positioned beneath the dichroic filter 159 as illustrated in FIG. 1A. A conventional objective lens of a stereo surgical microscope is configured to perform in the visible spectrum. OCT uses the infrared spectrum. Thus, the objective lens 159 in accordance with embodiments discussed herein may be modified to extend the wavelength range of the objective lens to allow imaging using OCT and improve the images provided by the surgical microscope using OCT. Furthermore, the objective lens 159 in accordance with embodiments discussed herein may be configured to be thinner than a conventional lens, thus, reducing the working distance. Details of the objective lens are discussed in commonly assigned U.S. Patent Application Publication No. 2013/0265545 to Buckland et al., entitled Surgical Microscopes Using Optical Coherence Tomography and Related Systems and Methods, the contents of which are hereby incorporated herein by reference as if set out in their entirety.

Referring again to FIG. 1A, as further illustrated the sample arm path 108 is coupled to an input beam zoom (IBZ) 150, a telecentric scan assembly 151, a beam expander 152 and an optional back focal length adjuster 154 which provide the beam to the modified dichroic filter 156 integrated into the surgical microscope. The beam travels through the dichroic filter 156 and into the objective lens 159 to image the sample 199, which may be an eye in some embodiments.

The input beam zoom (IBZ) 150 is provided for input beam shape control. Details of IBZs are discussed in detail in commonly assigned U.S. Patent Application Publication No. 2013/0141695 to Buckland et al., entitled Optical Imaging Systems Having Input Beam Shape Control and Path Length Control the entire contents of which is hereby incorporated herein by reference as if set forth in its entirety.

The telecentric scan assembly 162 controls the telecentricity of the system. For example, the telecentric scan assembly 162 in accordance with some embodiments may include a telecentric galvo relay lens (GRLs) pair, i.e. a first GRL half (GRLH) and a second GRLH. Each GRLH may be designed as a modified Wild eyepiece. However, telecentric scan assemblies 162 are discussed in detail in commonly assigned U.S. Patent Application Publication No. 2013/0141695 to Buckland et al., the entire contents of which was incorporated herein in its entirety above.

The beam expander 154 (relay beam expander (RBE)) is an afocal RBE system, the details of which will be discussed further below. The objective back focal length adjuster 154 provides adjustment to a range of main objectives. Thus, embodiments of the present inventive concept provide an OCT system having an objective lens that can adapt to changes in focal length. In other words, typically when the focal length is adjusted at the front, it also needs to be compensated at the back, i.e. back focal length adjustment.

Although the RBE 152 and the objective back focal length adjuster 154 are illustrated in FIG. 1A as separate modules, embodiments of the present inventive concept are not limited to this configuration. For example these two modules 152 and 154 may be combined without departing from the scope of the present inventive concept. Similarly, although the various modules of FIG. 1A are illustrated as separate blocks, these blocks can be combined or separated into more blocks without departing from the scope of the present inventive concept. The OCT system illustrated in FIG. 1A is a system that is optimized for telecentric imaging of the anterior segment of the eye of a subject or other structures directly accessible and visible to the surgical microscope.

Surgical microscopes in accordance with some embodiments of the present inventive concept include an "infinity space." This is a space above the final objective lens before the stereo beams converge. For example, in FIG. 1A, the dichroic filter 256 is inserted into this "infinity space." This space with one or more spectrally diverse or polarization diverse filters may be used to couple additional accessories to the surgical microscope system. Accessories may include, but are not limited to, for example, a video camera, wavefront analysis system, an auto refractor, a scanning laser ophthalmoscope and/or a laser. In some cases the coupling element will be within the infinity space, but in some cases a coupling element may exist elsewhere in the OCT signal path.

Figure 1B:
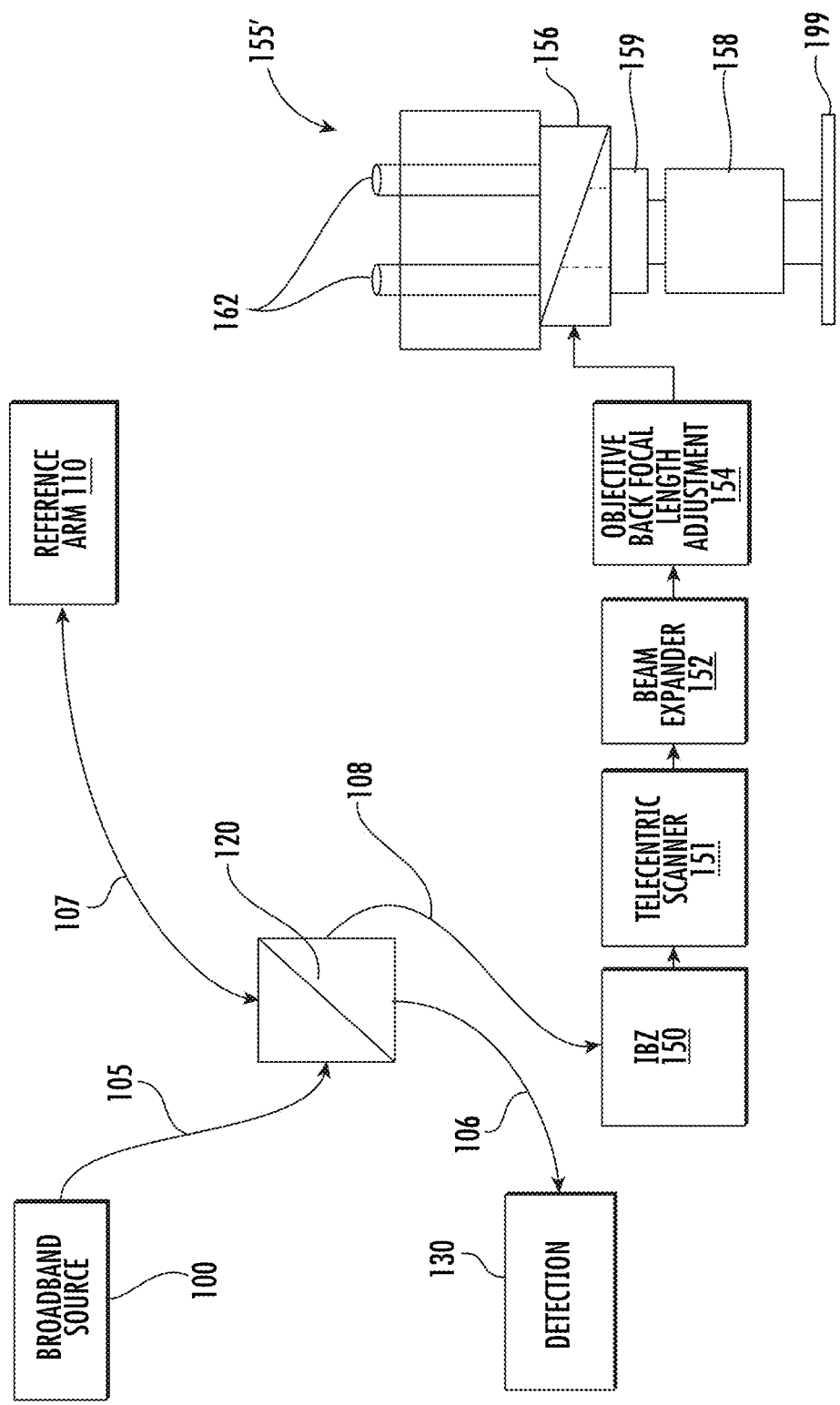
FIG. 1B is a block diagram of a surgical microscope that may be used in accordance with some embodiments of the present inventive concept.

Referring now to FIG. 1B, a block diagram of an OCT surgical microscope in accordance with some embodiments of the present inventive concept will be discussed. Like reference numbers in FIG. 1B refer to like elements in FIG. 1A, thus, details of these elements will not be repeated in the interest of brevity. As discussed above, it is quite common to use an intermediate lens, such as the Binocular Indirect Ophthalmo Microscope (BIOM) of Oculus Optikgerat, to relay the image of the retina to the surgeon. This intermediate lens is mounted to the under-carriage of the microscope head, and includes mechanics to adjust focus, and to flip the lens into and out of the field of view of the microscope. The BIOM is a retinal imaging lens that allows the microscope to switch between viewing anterior and posterior structures of the eye. However, the BIOM retinal lens is not optimized for use with OCT and thus an improved retinal lens is needed for use with an OCT surgical microscope.

As illustrated in FIG. 1B, a retinal lens 158 (surgical retina lens assembly) in accordance with some embodiments of the present inventive concept is positioned beneath the objective lens 159. The retinal lens 158 is modified as discussed in commonly assigned U.S. Patent Application Publication No. 2013/0265545 to Buckland et al. for optimized use with OCT and is configured to adjust accordingly. As discussed therein, the retina lens (surgical retina lens assembly) includes a condenser and a modified retina lens. The retina lens allows the focus to be moved down to the retina.

It will be understood that the surgical microscope should be as compact as possible to allow enough room for the surgeon to perform the procedure between the objective lens of the microscope and the sample/patient. In other words, there needs to be a reasonable working distance between the patient and the microscope so the surgeons' hands can comfortable perform the procedure. Accordingly, in some embodiments the dichroic filter and the OCT portion of the OCT surgical microscope may be provided in a center channel of the surgical microscope itself.

To summarize, in some embodiments of the present inventive concept, a spectral domain OCT (SDOCT) system operating in the 800 nm-900 nm spectral range is used for imaging. In these embodiments, the SDOCT may use a superluminescent diode having a 3 dB bandwidth of 93 nm centered at 860 nm. The source is coupled through a single-mode optical fiber to a fiber splitter, wherein 80% of the optical power is directed to a reference path and 20% of the optical power is directed to a sample path.

The reference path includes an optical fiber delivery to a collimated output, the collimated output is delivered to a retro-reflecting mirror, and the reference signal is thereby coupled back into the reference path transmitting back towards the fiber splitter. The reference mirror construction includes a variable path length adjustment, suitable for coarse adjustment such that the path length to the reference mirror is equal to the path length through the sample path to the region of interest in the sample. The reference path length adjustment is finely controllable to position the relative offset of the reference reflection to the sample structure to within approximately 0.1 mm or finer. The reference arm may include a variable attenuator to control the optical power level of the returned light, and may include a birefringence or polarization control element.

The sample path includes an optical fiber delivery to a collimated output; the collimated output is delivered to scanning system and imaging optics relevant to the surgical application. An example configuration is discussed in U.S. patent application Publication Ser. No. 13/836,576 to Buckland et al., which has been incorporated herein by reference above. As discussed therein, the collimated output is directed to an optical beam focus and magnification controller to a telecentric scanner assembly, to a beam shaping telescope, through a dichroic filter that couples the OCT signal to a microscope imaging path, sharing a common final objective. The beam focus and magnification control allows for managing the location of focus of the OCT beam relative to the microscope focus, and allows further for controlling a magnification of the beam. The magnification of the beam is useful for controlling an apparent depth of field as the uniformity of brightness across the depth will vary with beam magnification. There are incidences where the highest lateral resolution is desired. There are incidences where the brightness is preferably shifted away from hyper-reflective surfaces. Independent control of focal position and brightness creates imaging flexibility that may therefore be tailored to address specific imaging requirements.

The optical power delivered to the subject is controlled to maintain eye safe illumination, in the case of ophthalmology, according to standards developed for the art. Eye safe illumination is a function of wavelength, focal spot size (radiant intensity) and exposure duration. The ability to control focal position and beam magnification provides further ability to dynamically control illumination levels, in order to maintain eye safety during long continuous exposures that might be desired during a surgical procedure. For example, a continuous scan may be acquired with beam parameters set for a particular safety level, so that the surgeon does not need to make a call to the software until a particular interaction sequence is desired. The beam focus may be offset away from the sample, or spot size increased to reduce intensity, allowing the acquisition and display of a useful, if less detailed image during portions of the surgical procedure, and returning to a more precise illumination condition when desired.

The signal returned from the sample, which may be polarization controlled, is mixed with the signal from the reference arm at the fiber splitter/combiner to create a spectral interferogram in the detector path. The detector path may include a single-mode fiber that delivers the interference signal to a dispersive spectrometer. Spectrometers appropriate to the application are discussed, for example, in U.S. Pat. Nos. 8,189,192; 8,310,674; and 8,348,427; and in U.S. patent application Publication Ser. No. 13/428,247 to Saxer et al., the disclosures of which are hereby incorporated herein by reference as if set forth in their entirety.

In order to produce a system with sharpest axial resolution for a given source bandwidth, the reference and sample paths should be well dispersion matched. It is not possible to physically match the dispersion using only hardware when the subject being imaged is variable, and the region of interest within a subject is variable. In such circumstances, software dispersion compensation, as discussed in, for example, U.S. Pat. No. 7,719,692, may be deployed to optimize image resolution. When multiple subjects or regions of interest are to be imaged, or multiple different objective lenses are to be used in imaging, it is further desirable to include pre-set dispersion optimization parameters within the software relevant to the hardware and subject in order to directly process images using appropriate dispersion correction parameters. Methods for managing and carrying out such subject-specific dispersion management are discussed in, for example, U.S. Pat. No. 8,401,257.

For ophthalmic anterior segment imaging, it is also often desirable to increase image depth while maintaining fine axial resolution. The broad class of Fourier domain OCT systems is known to create an image and its complex conjugate that in general carries no unique information. The presence of the complex conjugate image limits the available image depth due to mirror images folding over each other. Techniques are now known for reducing complex conjugate ambiguities. One such technique for spectral domain OCT is discussed in, for example, U.S. Pat. No. 7,742,174. Other techniques and reference arm switching provides an alternative technique for increasing image depth, as discussed in, for example, U.S. Pat. Nos. 8,625,104 and 8,425,037.

The utility of providing three-dimensional OCT images to the surgeon extend beyond simple visualization. A well calibrated OCT system offers three-dimensional measurement capability that can be used to provide additional guidance to the surgeon, including the determination of relevant derived clinical parameters, relevant to the outcome of the surgical procedure. For imaging of the cornea, OCT derived data is useful for computing many common refractive parameters, as discussed in, for example, U.S. Pat. No. 8,693,745.

The combination of imaging, processing, and computational technologies associated with Fourier domain OCT in general, and spectral domain OCT and swept source OCT specifically, provides the foundation for a high-value procedural imaging system for use in ophthalmic surgeries. One class of procedures of high clinical importance is cataract surgery. Intra-surgical OCT offers a unique capability to provide enhanced surgical guidance, provide in situ metrology to improve refractive outcomes, and analyze involved tissues in structures to reduce associated risks as will be discussed further below with respect to FIGS. 2-21.

Figure 2:
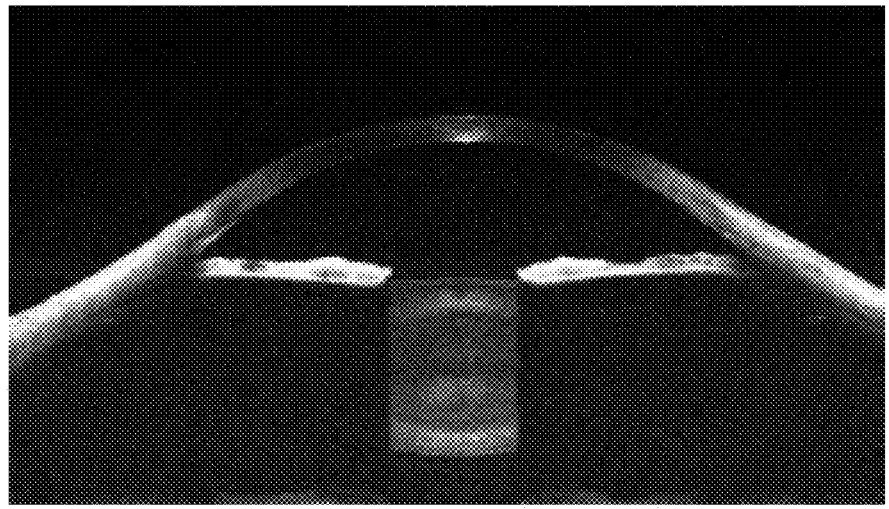
FIG. 2 is an image illustrating a 15 mm full anterior segment image.

Referring now to FIG. 2, an example of a deep imaging spectral domain OCT image of the anterior segment of a human eye will be discussed. The spectrometer used in the particular system is a wavenumber-linearized design as discussed in, for example, U.S. Pat. No. 8,348,427 and U.S. Patent Application Publication No. 2012/0242988, with a 15 mm single-sided (not complex conjugate resolved) depth as measured in air. The axial resolution is 8 micrometers, and the FOV is 20 mm. The image is acquired with a CMOS linescan camera having an array of 4096 pixels. Images are acquired, processed and displayed at 20,000 lines per second.

Figure 3:
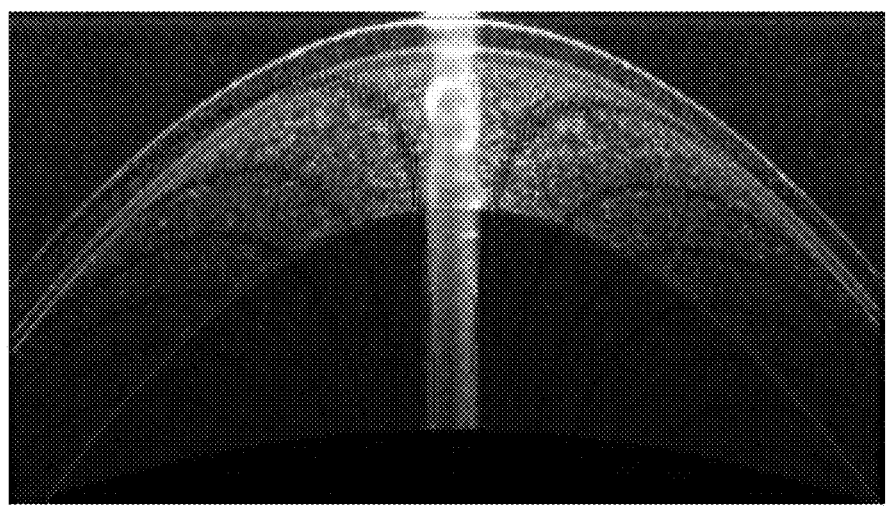
FIG. 3 is an image illustrating a high resolution cross section of a cornea with a contact lens.

FIG. 3 illustrates an example of a high resolution spectral domain OCT image of the cornea of a human eye. The image illustrated in FIG. 3 includes a contact lens over the eye. The spectrometer used in the particular system is as discussed in U.S. Pat. Nos. 8,189,192 and 8,310,674 with a 3.4 mm single-sided (not complex conjugate resolved) depth as measured in air. The axial resolution is 3.5 micrometers, and the lateral FOV is 6 mm. The image is acquired with a CCD linescan camera having an array of 2048 pixels. Images are acquired, processed and displayed at 32,000 lines per second.

In FIG. 3, an automated layer segmentation algorithm using one a variety of methods known in the art is applied to the image to locate the anterior surface of the contact lens, the contact lens to epithelium boundary, Bowman's layer, and Descemet's layer of the cornea. Additionally, the image is corrected for beam refraction at the air-to-lens interface, as discussed in, for example, U.S. Pat. No. 7,072,047. Such layer segmentation provides the base dimensional information for computing clinical parameters, such as surface curvature, layer thickness, and refractive power. When the boundary layers are derived for a surface, additional clinical information, including optical aberrations associated with a particular layer, a particular structure (cornea or lens) or the combined optical system of the anterior segment of the eye may be derived.

Figure 4:
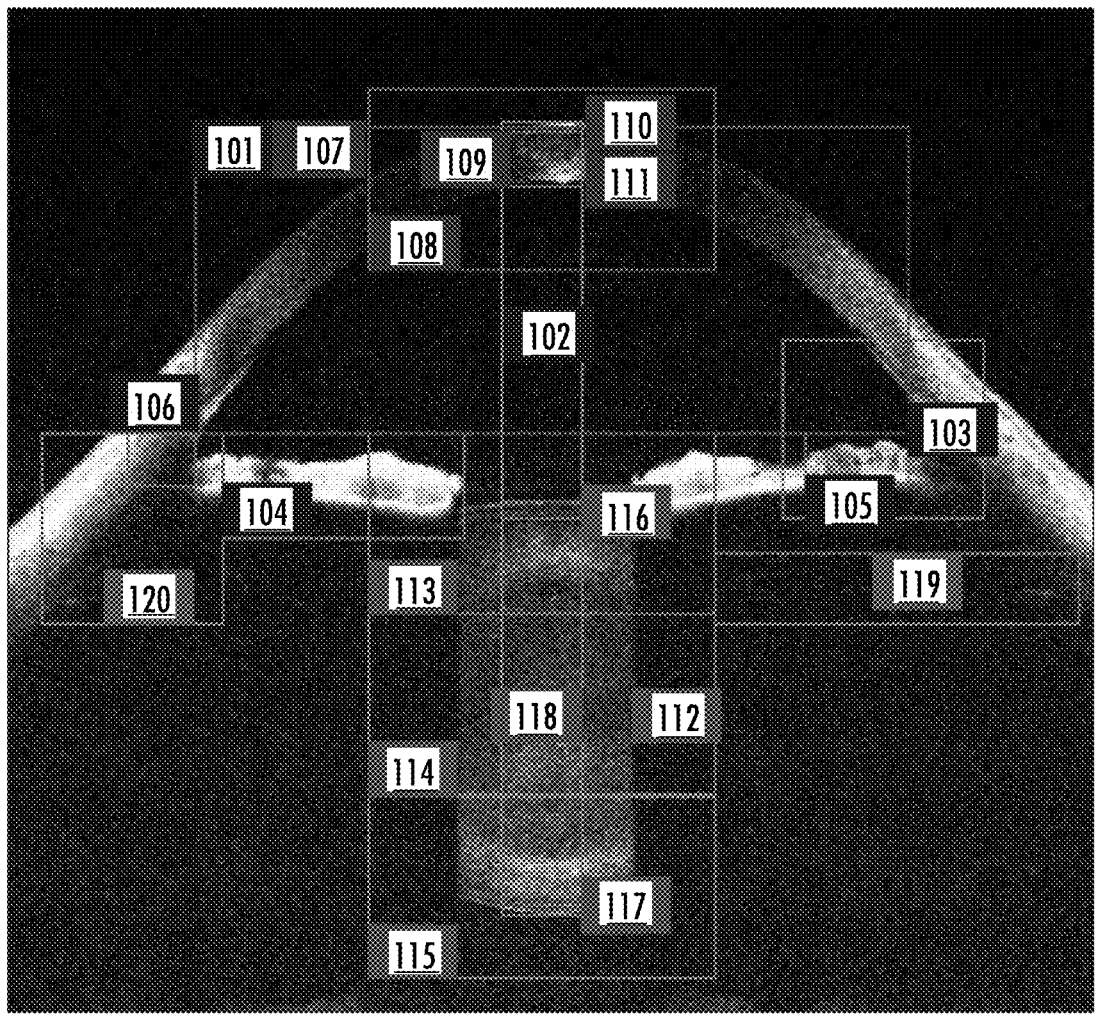
FIG. 4 is a diagram illustrating various portions of the human eye.

FIG. 4 illustrates various structures of the anterior segment that may be imaged, visualized or measured during ophthalmic surgery. Structures include: 101) an anterior segment; 102) an anterior segment depth; 103) an iridocorneal angle; 104) an iris; 105) vascularity in an iris; 106) Schlemm's Canal; 107) a cornea; 108) a visual field of a cornea; 109) an apical cornea; 110) the epithelium and Bowman's layer of a cornea; 111) a stroma and Descemet's layer of a cornea; 112) a crystalline lens; 113) an anterior portion of a crystalline lens; 114) a central portion of a crystalline lens; 115) a posterior portion of a crystalline lens; 116) an anterior lens capsule; 117) a posterior lens capsule; 118) a lens thickness; 119) zonules in the posterior chamber; 120) a ciliary process in the anterior chamber.

One value of the depth-resolved imaging capability of OCT that is not offered with even 3D surgical microscopes is the ability to assess the relative orientation of structures in the eye. FIG. 5A provides an example relevant to refraction in the eye. The visual axis of the crystalline lens (vector a) is compared to the visual axis of the apical cornea (vector b). Though shown for illustrative purposes only, these axes are not in general in perfect alignment. OCT affords the opportunity to assess the visual alignment of the cornea to the natural crystalline lens, or the cornea to phakic lens to crystalline lens, or cornea to pseudophakic lens.

Figure 5B:
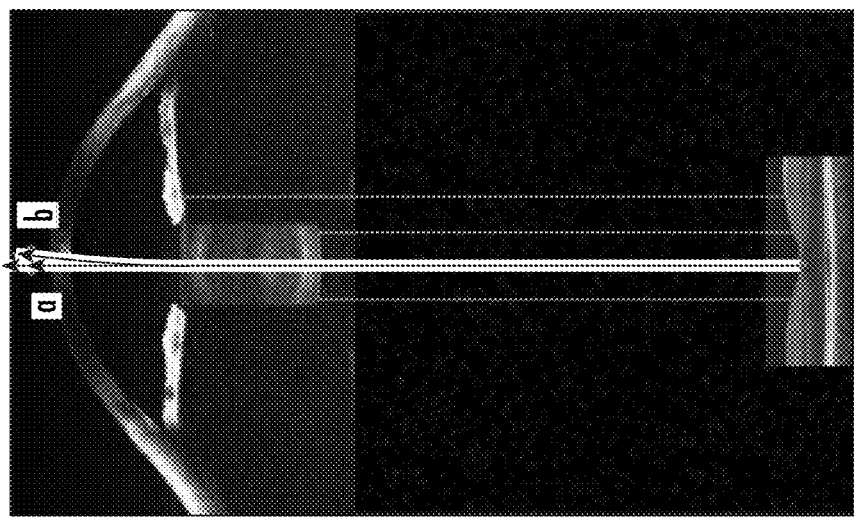
FIGS. 5A and 5B are scans produced in accordance with some embodiments of the inventive concept.
Figure 5A:
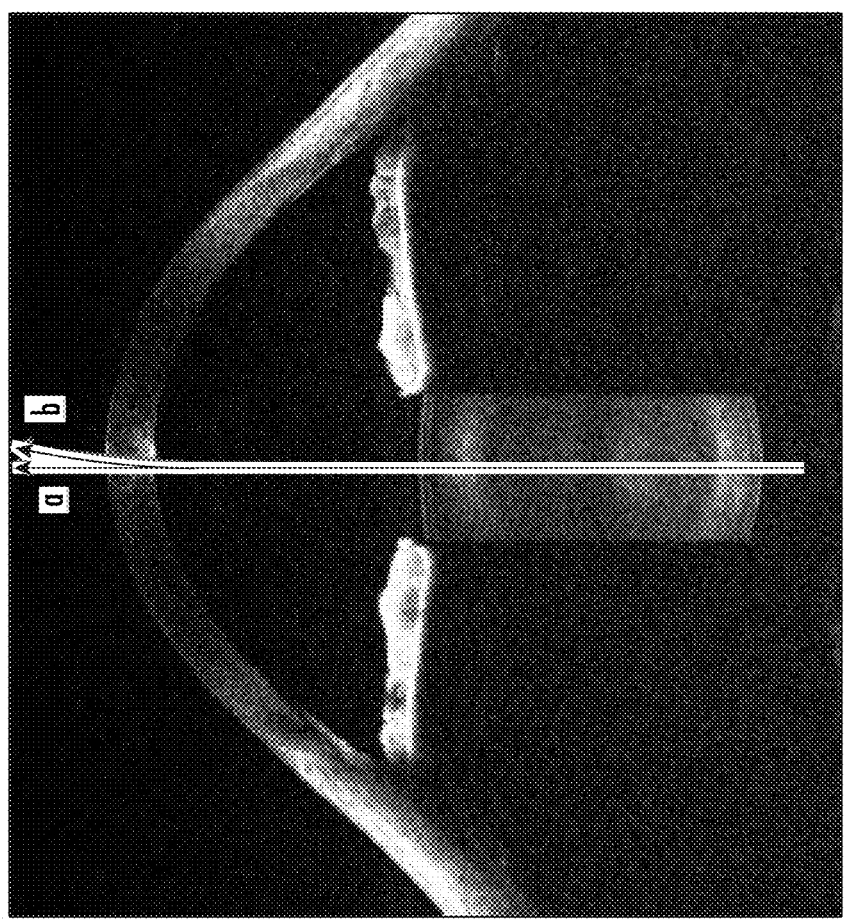

Furthermore, some embodiments of the present inventive concept include a reference arm with sufficient range to move the imaging plane from the anterior segment to the posterior pole, or macular, as illustrated in FIG. 5B. In order to acquire an image of the macula without introducing supplementary optics, two actions are undertaken: first, the focus must be changed from an anterior focus to a posterior focus. For a surgical system with a working distance of 175 mm and corresponding objective lens, −5.7 Diopters (D) of adjustment are required to move the OCT beam from focusing on the cornea to a collimated beam that will be focused on the retina of a well-corrected subject.

The focal power of the cornea and lens are subject specific, but are in the range of 43 Diopters and 15 Diopters for the average human cornea and lens, respectively. For an aphakic subject missing a natural or replacement lens, an addition of 15 Diopters to the focal power of the OCT beam will be required from the collimated state to image to the retina.

The input beam zoom that manages the focus and magnification does not change the sample arm path length. In order to image the posterior pole, the focus is adjusted to the expected refractive state for the eye, given the microscope objective and refractive condition of the eye. The reference arm path length is modified for the expected eye length of the eye. For a well corrected eye, the input beam zoom will shift from 0 D to −5.7 D (power of 175 mm focal length objective) to shift focus from cornea to retina. For a physical eye length of 24 mm, the optical eye length, assuming a path averaged refractive index of 1.38, will be 33 mm. The reference arm will lengthen 33 mm to move the image from the cornea to the retina, as the focus is commensurately changed. No change in working distance, i.e. no physical change between the imaging system and the subject, is required.

An actual subject will have a different eye length and an imperfect refraction. Furthermore, the subject may have perturbations to shape of the macula, and aberrations in refraction. A control loop combining scan area, reference arm path length, and focal control can effectively map out structural and optical characteristics of the eye in situ, with a posterior FOV limited only by the aperture of the iris, which is generally well dilated during a surgical procedure. In fact, because of the wide dilation of the eye, mapping the eye in this manner during a surgical procedure may provide significantly greater information than in a traditional office examination.

One control loop to map out the eye may proceed as follows: The input beam focus is set to 0 D and the reference arm set for anterior cornea surface imaging. A first image set of the cornea is acquired. The scan beam is set to image the apex or apical region of the cornea. In a coordinated fashion, the beam focus is set to increasingly decreasing dioptric powers and the reference arm is lengthened to position the acquisition at increasing depths until the expected position of the macula is reached. Data is acquired throughout the control sequence and data is stored with positional information from the focal control and reference control units. Data is acquired at the camera line rate. Speed of the control loop is limited by the physical movement of the reference arm mirror over the eye length and by the focal control. Assuming a 36 kHz linescan camera and a stepper motor with 50 micrometer precision and 1000 steps per second, the reference arm will move at approximately 50 mm per second. The total acquisition will take just over one-half second, and approximately 18,000 lines of data will be acquired. This large number of data samples makes registering data at each longitudinal position very precise.

This control loop may be repeated, extended, or modified in many ways. One approach is to acquire a finite, small, number of such lines-of-site that map out pillars of the structure of the eye to the degree that the field of view allows. A useful such map would place line-of-site pillars along a Cartesian or polar grid, for example on four quadrants in two rings, for a total of nine pillars, including the center. A complete such acquisition, without optimization, would take less than 5 seconds.

Image processing is used to identify a boundary surface of the macula. This processing may be accomplished in the spatial domain after Fourier transform of the spectral data. This processing may also be accomplished directly in the spectral domain, as the transition from posterior chamber to retinal tissue will result in a transition from a non-interfering to an interfering condition, wherein the peak spectral system will increase. Once the retina is identified, the surface is brought to a target position within the Fourier domain spatial window. At this point, the refraction is determined by optimizing focus to increase image brightness. The positional sensitivity of this optimization may be enhanced by increasing the beam magnification at the input beam control device, thereby increasing the imaging numerical aperture and reducing the depth of field.

The offset in input focus from the collimated state will correlate directly to refractive error in the subject at the imaging position. The ocular dimension may be read directly from the reference arm change, adjusting from refractive index, and monitoring the surface positions in the OCT window at beginning and end points of the scan. The longitudinal scans themselves can be registered, as suggested above, and form a self-referenced data set that will provide a very accurate length measurement. In these two complementary approaches, a very accurate biometry and refraction of one line-of-site in the eye is rapidly acquired.

Optimization loops will add some time, depending on the degree of precision desired. Focus and reference position do not need to be coupled, but can be optimized separately. An efficient procedure will involve first setting a reference position to set the sample image at a desired position within an image window, followed by a brightness-based focus optimization. Focus may be optimized to approximately 0.25 D in ten or fewer steps, and may take less than a few seconds.

Since time of acquisition is limited by mechanical position controls, rather than scanners or data acquisition, the first axial-priority loop may be supplemented by lateral priority scans to acquire image sections that can be aggregated to create a full three-dimensional model of the eye.

These axial structural and refractive imaging steps may be complemented with a series of other structural images and derived computations. At each structural element, for example cornea and lens, a series of cross-sections may be acquired to create the structure of a volumetric image. These cross sections may represent a relatively low density sampling of the structure, or may be highly sampled, sufficient to fully sample at the optical resolution, to create a high definition volumetric image of the structure. During surgery, the subject is generally still and artifacts of motion reduced, but there may be breathing or other vibrational artifacts present. Registration techniques may be applied to reduce or eliminate residual artifacts of motion. From the volumetric structures, boundary layers are segmented using filtering and layer identification techniques and surfaces constructed. From the surfaces, curvatures are computed and distances between layers computed. This information provides sufficient information to compute optical properties of layers and structures, including refractive powers and aberrations. In contrast to autorefractors and aberrometers, the computed refractions and aberrations, particularly in concert with the structural and refractive information derived all the way to the macula, allow for assessment of the contributions of ocular performance from independent layers and structures in the eye, and thus provide the surgeon with a degree of information and guidance not possible with the purely functional measures from an autorefractor or aberrometer.

Figure 6:
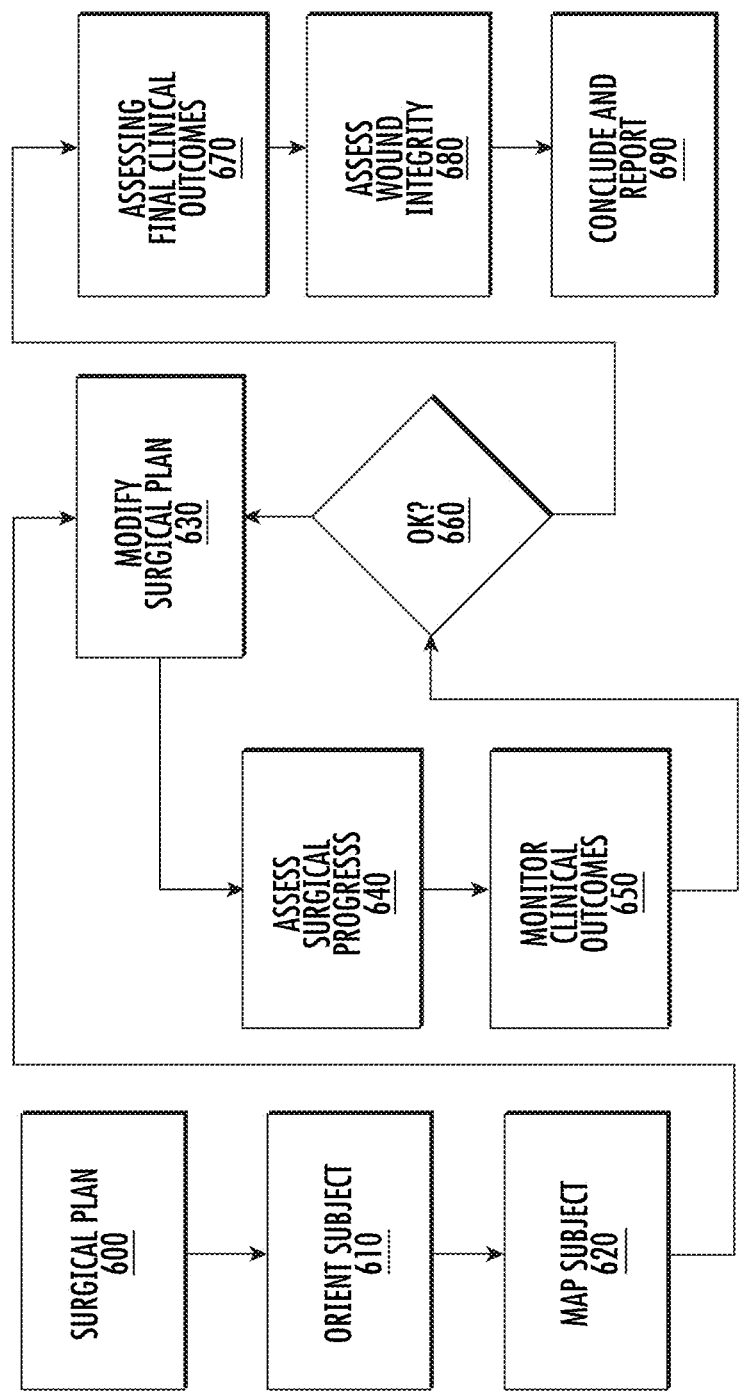
FIG. 6 is a flow chart illustrating operations in a general surgical imaging procedure.

These controls and measures may be combined in a series of steps that provide in situ guidance to the surgeon with images and measurements not available in any other way. Referring now to FIG. 6, a general workflow for a surgical procedure incorporating OCT will be discussed with respect to the flow chart of FIG. 6. Operations begin at block 600 by starting with a surgical plan. The surgeon uses OCT to confirm patient orientation, for example, to confirm that the eye under test is correct (block 610). A structural map of the subject is obtained, and relevant clinical parameters are computed from the OCT (block 620). The relevant clinical parameters may include, for example, measures of cornea total thickness, measures of the thickness of the epithelium or endothelium, central ore average curvature of the anterior or posterior structures of the cornea or the individual layers of the cornea, local curvatures across the field of view of these structures of the cornea, computations of the average and local refractive powers of the cornea, functional shapes of the corneal surfaces, measures of optical aberrations, measures of the sphere, cylinder, and angle of the cornea that define the first and second order keratometric state of refraction of the eye, similar measures of the crystalline lens or any artificial lenses paced with the eye, and similar composite measures of the optical system comprised of the cornea and all natural and artificial lenses placed within the visual field of the eye. Additional clinical parameters may include the irido-corneal angle, sclera thickness, conjunctiva thickness, dimensions of Schlemm's canal, Doppler measures of flow rates through schlemss canal and through blood vessels in the sclear and conjunctiva and in vessels that have ingressed into the cornea, and measures of nerve fibers that have ingressed into the cornea. Additional parameters may be relative or absolute opacities of pathologic structures, and dimensional measures of pathologic structures. This is a partial list of clinical parameters that may be measurements enabled by the depth resolved and superficial imaging of OCT, relative opacities and textures that may derived from the large dynamic range of the OCT image, the phase-dependent capabilities of OCT from which for example Doppler flow images are derived, spectroscopic capabilities of OCT that are derived from the broadband nature of the OCT light source, and derived attributes that may be computationally assessed based on such measurements derived from the OCT images and processed to derived functional parameters from the structural parameters (such as computing refractive power from the combination of thicknesses and curvatures).

If necessary, the surgical plan may be modified (block 630). The surgical process is assessed at intermediate intervals (block 640). For example, the surgical process may be assessed by measuring the change in thickness or shape of particular surface or layer of a structure, measuring the depth width or thickness of an incision, observing or quantifying flow through an incision, observing or measuring surgically induced edema or tears. Clinical outcomes are tested at intermediate intervals (block 650). If it is determined that the surgical plan needs to be modified based on the various assessments (block 660), the surgical plan is modified according to OCT information by returning to block 630 and repeating until it is determined that the surgical plan no longer needs modification (block 660). The final clinical outcomes are assessed (block 670). Wound integrity and damage or stress to surgical site or neighboring tissues is assessed (block 680). Assessing wound integrity may include, for example, assessing degree of closure of an incision or observing the flow through an incision as is discussed further below. The surgical process is concluded, and report generated (block 690).

Figure 7:
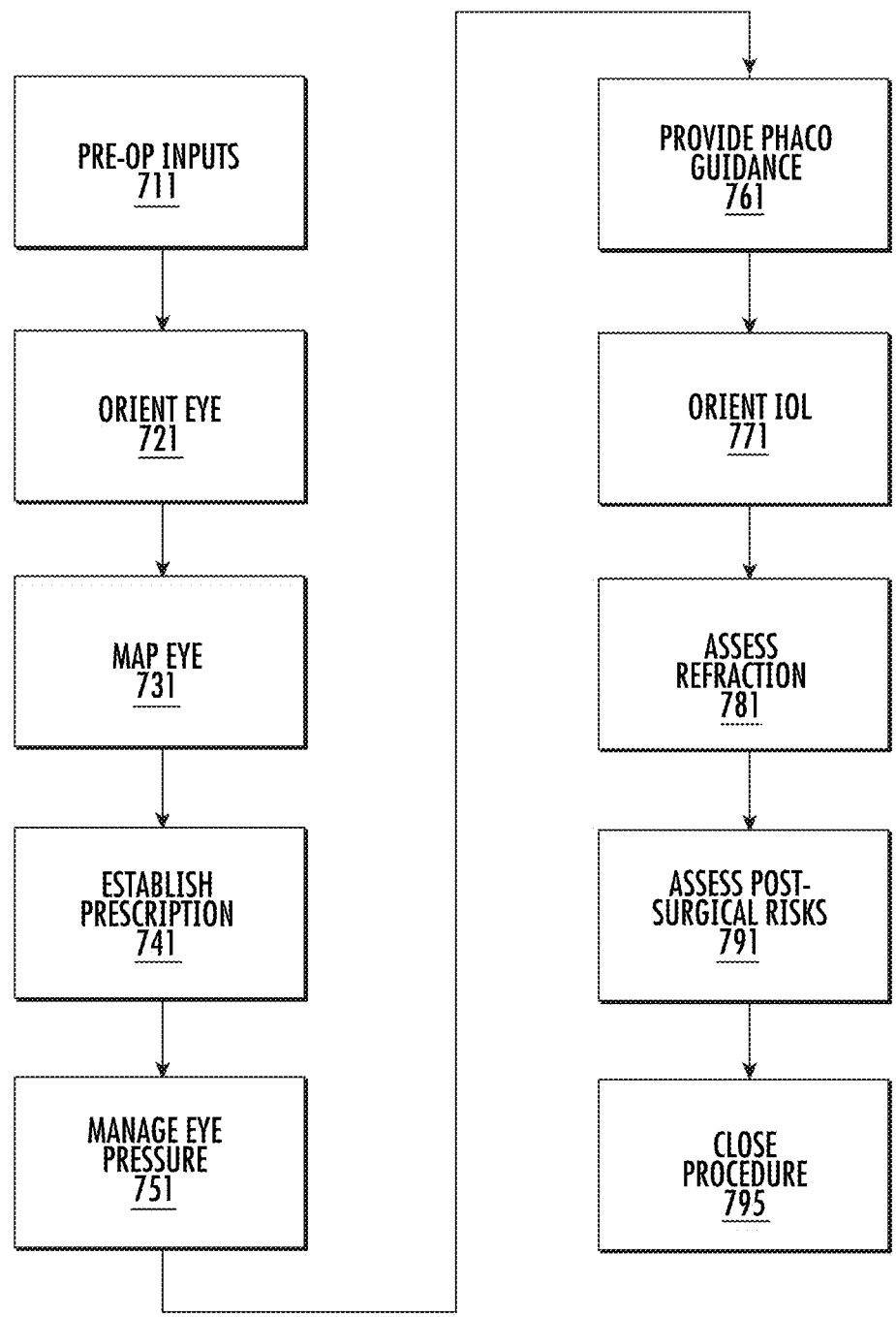
FIG. 7 is a flow chart illustrating general operations in a cataract procedure in accordance with embodiments of the present inventive concept.

Operations for a specific procedure for imaging applied to cataract surgery will now be discussed with respect to the flow chart of FIG. 7. As illustrated therein, operations begin at block 711 by confirming a surgical plan and pre-operative inputs. The eye is imaged and the correct eye (OD/OS) is confirmed (orient eye) (block 721). As used herein, "OD" refers to oculus dexter and "OS" refers to oculus sinister (FIG. 8B), which are Latin terms for right eye and left eye, respectively.

Figure 8B:
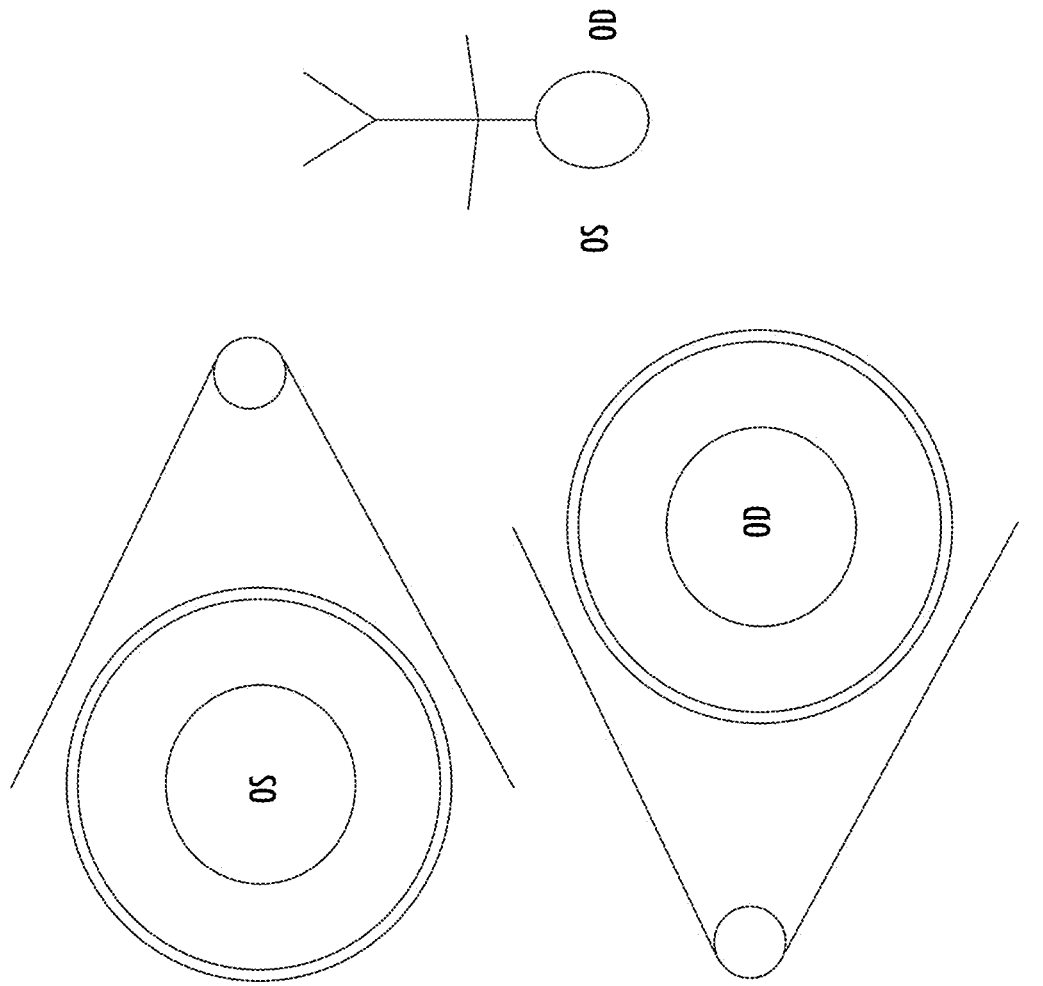
FIGS. 8A and 8B are a flow chart and diagram, respectively, illustrating operations in orienting the eye in accordance with embodiments of the present inventive concept.
Figure 8A:
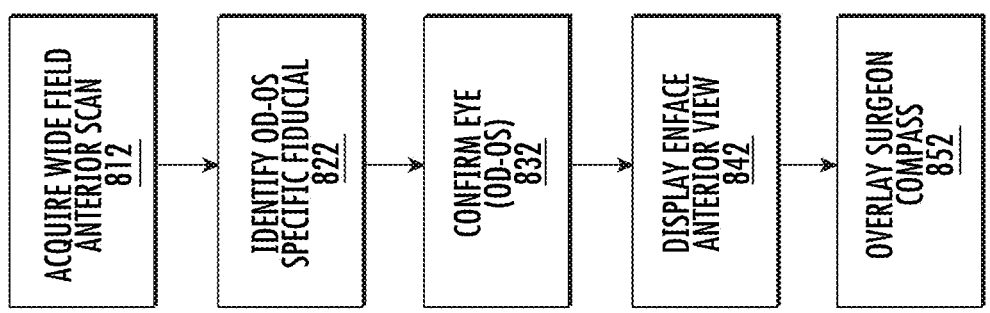

Operations for orienting the eye will now be discussed with respect to the flow chart of FIG. 8A. As illustrated therein, orientation may be accomplished by obtaining a wide angle view (block 812), observing anterior structures within approximately 25 mm nasally and temporally with respect to cornea apex (block 822), and identifying presence of the lacrimal punctum to confirm the eye (block 832). There are two lacrimal puncta in the medial (inside) portion of each eye. Together, they function to collect tears produced by the lacrimal glands and when observed provide visual evidence of the specific eye under test.

Other landmarks may be identified in the sample, defined and used in orientation, including imaging to retina and observing optical nerve head or trajectory of retinal vasculature. For visualization, an en face projection image may be created and displayed for the surgeon (block 842). The en face view may include an orientation graphic, or compass, which orients the surgeon to the surgeon's accustomed view. This view will be referred to herein as "the surgeon's compass" (block 852). Key structures of the en face view may be segmented and displayed for rapid orientation, including a circle or ellipse defining the iris, a circle or ellipse defining the cornea, and a direct segmentation, highlight, or graphical representation showing the lacrimal punctum location or direction.

Figure 9:
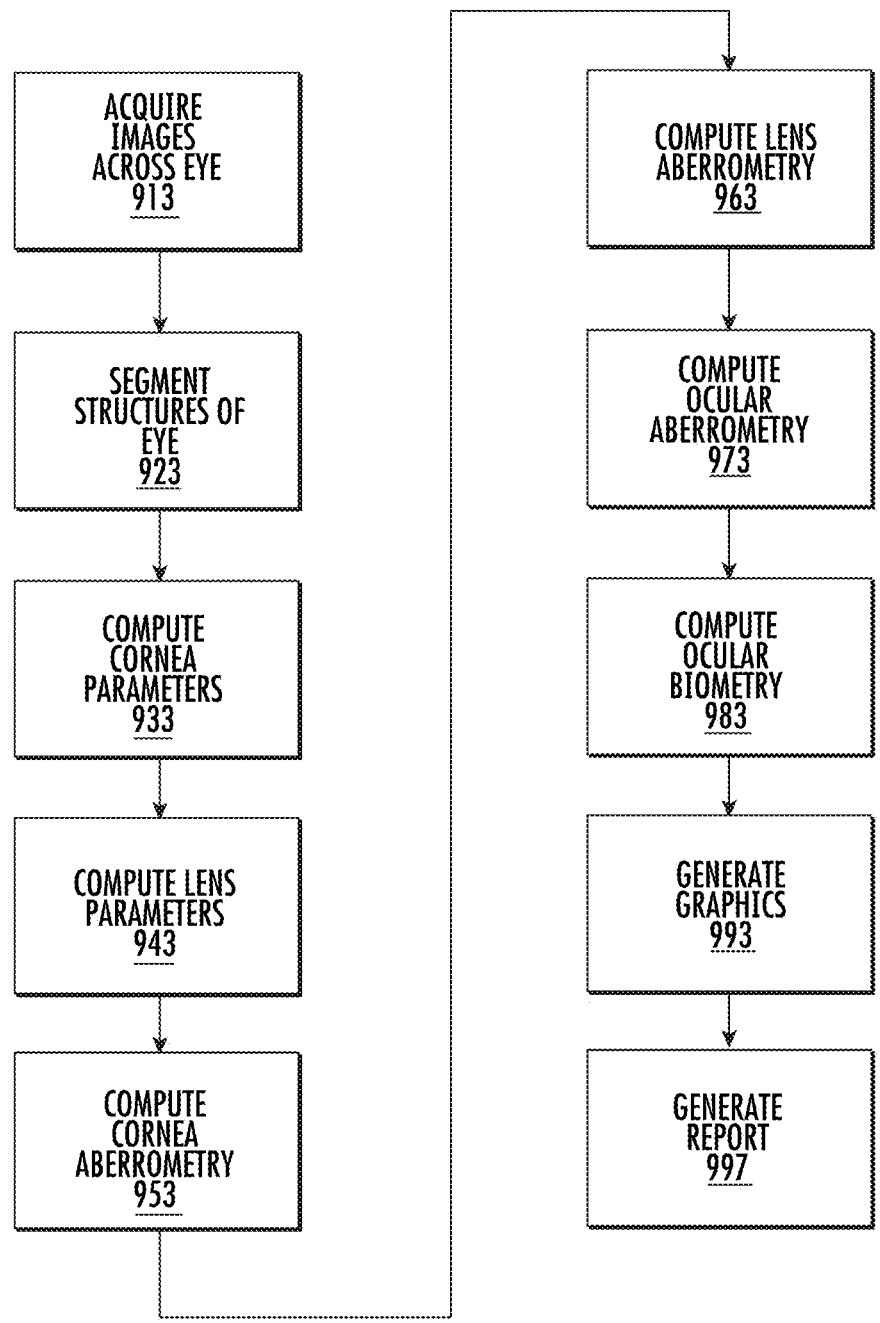
FIG. 9 is a flow chart illustrating operations in mapping the human eye in accordance with embodiments of the present inventive concept.

Referring again to FIG. 7, the eye may be mapped using technologies and techniques as described above (block 731), or other similar or related techniques that rely on the OCT image, as illustrated in FIG. 9. Referring now to the flow chart of FIG. 9, from the one or more acquired images of the eye (block 913), structures may be segmented (block 923), and clinical parameters derived (block 933), such as topography and pachymetry of the cornea and lens, and if desired, various layered structures within the cornea or lens (blocks 943, 953, 963, 973). From the structural segmentation, functional clinical properties such as refraction of cornea, lens and integrated optical system of the combined components may be derived. Using the axial range finding techniques described above, a full ocular biometry may be derived (block 983). A set of graphics including three-dimensional images, wire-frame models and en face projections aligned to the surgeon's compass view may be constructed to provide clarity for the surgeon (block 993), and a report of clinical parameters provided (block 997).

From at least this information, a prescription for the replacement IOL, and a target diameter for the capsulotomy may be established anew, or established and compared to the original prescription, and a surgical plan may be modified accordingly (block 741). As illustrated in FIGS. 10A and 10B, from the OCT data, refraction, including sphere, cylinder and toric orientation (blocks 1014, 1024 and 1034), as used to prescribe astigmatism correcting optics, and toric intraoculars lenses (IOLS), may be directly computed. The OCT-computed target refraction and orientation can then be displayed (solid arrows in FIG. 10B), for example on the en face surgeon compass view (block 1044). If an original prescription is provided, the OCT-computed prescription can be compared (block 1054) with the original prescription (dashed arrows in FIG. 10B), and the surgeon maintains responsibility for deciding on the final prescription. Graphics and reports may be generated (blocks 1064 and 1074).

Figure 11B:
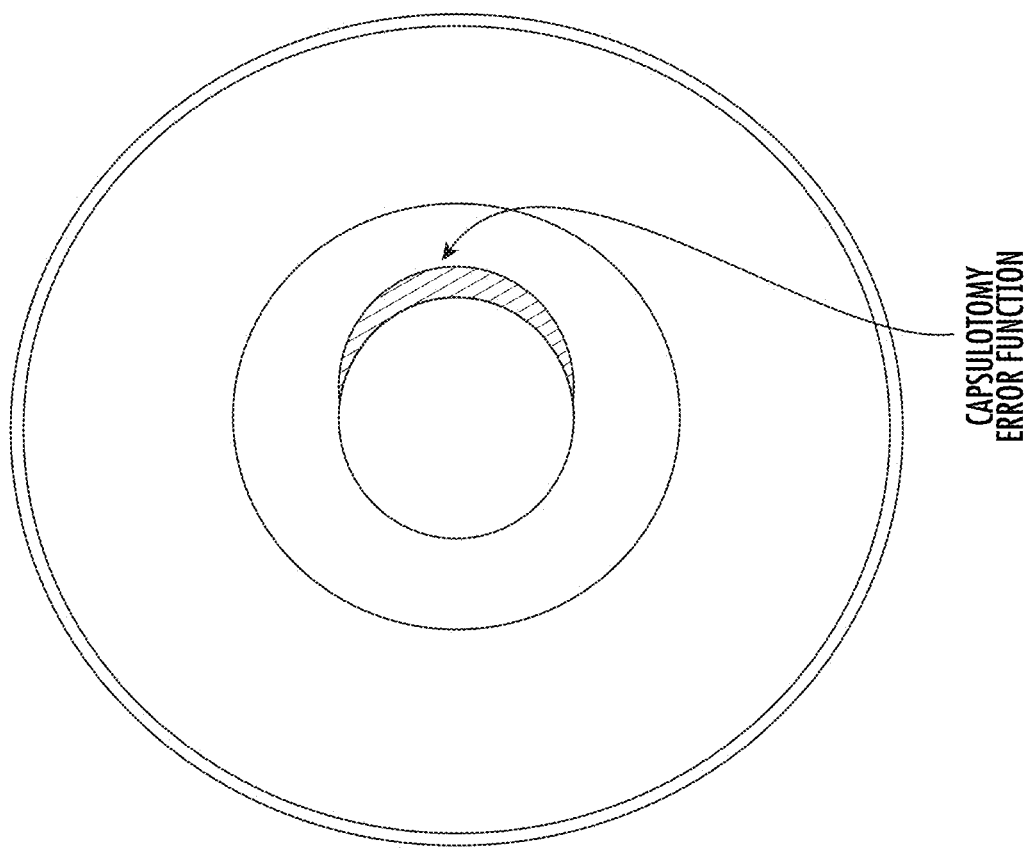
FIGS. 11A and 11B are a flow chart and a diagram, respectively, illustrating operations in providing capsulotomy guidance in accordance with embodiments of the present inventive concept.
Figure 11A:
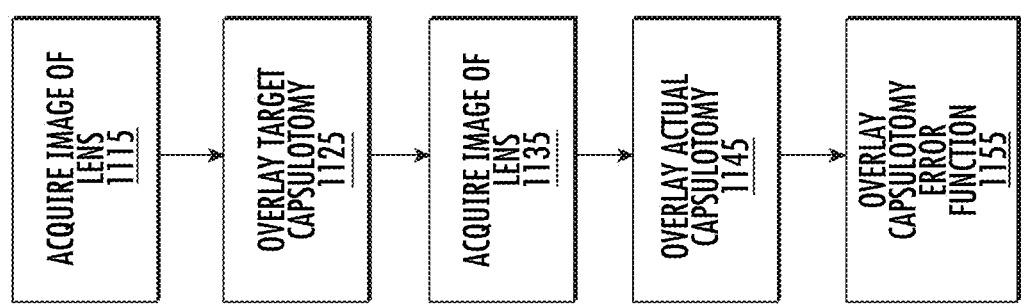

During the surgical procedure, surgical progress may be monitored by viewing OCT cross-sections and en face projections of various structures in the eye (block 751). An initial surgical step for cataract surgery is making a pair of initial corneal incisions. The OCT may be aligned to image these limbal incisions, and cross-sectional and en face views displayed to demonstrate wound quality, and assess tears. The next step is performing the capsulotomy prior to lens emulsification and extraction. As used herein, "capsulotomy" refers to the creation of access to the lens by opening a port in the capsular bag surrounding the lens. To perform a capsulotomy, operations begin at block 1115 of FIG. 11A by acquiring an image. A target size, shape and position may be displayed on the en face compass view (block 1125), and OCT images acquired (block 1135) continuously or intermittently, with the current shape of the capsulotomy highlighted against the target (block 1145), and an error function displayed to provide further guidance to the surgeon (block 1155). The capsulotomy error function is illustrated in FIG. 11B. In some embodiments, the system may be configured to provide an appropriately audible sound when the error function exceeds a pre-determined limit, providing the surgeon a chance to modify the procedure during the procedure to reduce the likelihood of error afterwards. In embodiments of the present inventive concept using laser capsulotomy, OCT is still useful to assess the resultant capsulotomy and capsule, identify the position of a floating capsulotomy or any incompletions in the perforations, again to provide more guidance to the surgeon.

Referring again to FIG. 7, operations proceed with performing phaco fragmentation (block 761). During phaco fragmentation, emulsification and extraction, OCT images may be continuously or intermittently acquired, allowing the surgeon to evaluate any risk to the capsular bag, and identify any abnormal stress transmitted to the zonules or other posterior structures. Towards the end of extraction, the OCT system may perform an important function in examining the capsular bag for residual epithelial cells that have the potential to lead to posterior capsular opacification (PCO), an adverse outcome that occurs in 25% to 50% of cases, requiring costly follow-up laser treatment.

Figure 12:
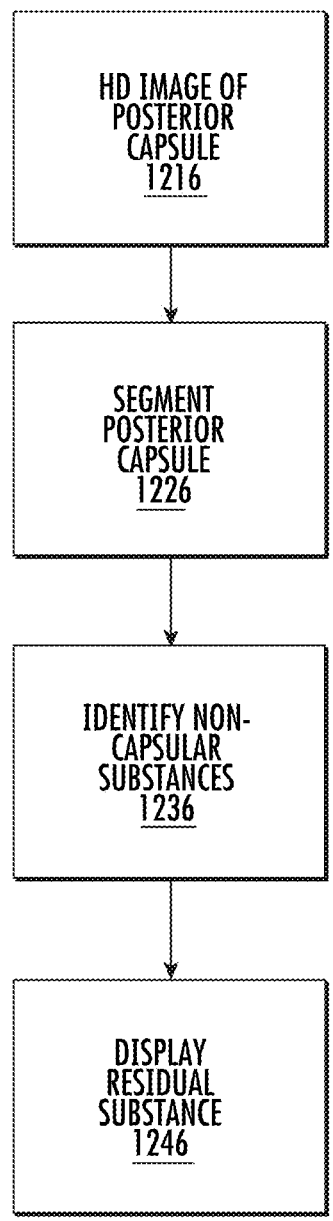
FIG. 12 is a flow chart illustrating operations in assessing the presence of residual epithelial in accordance with embodiments of the present inventive concept.
Figure 13:
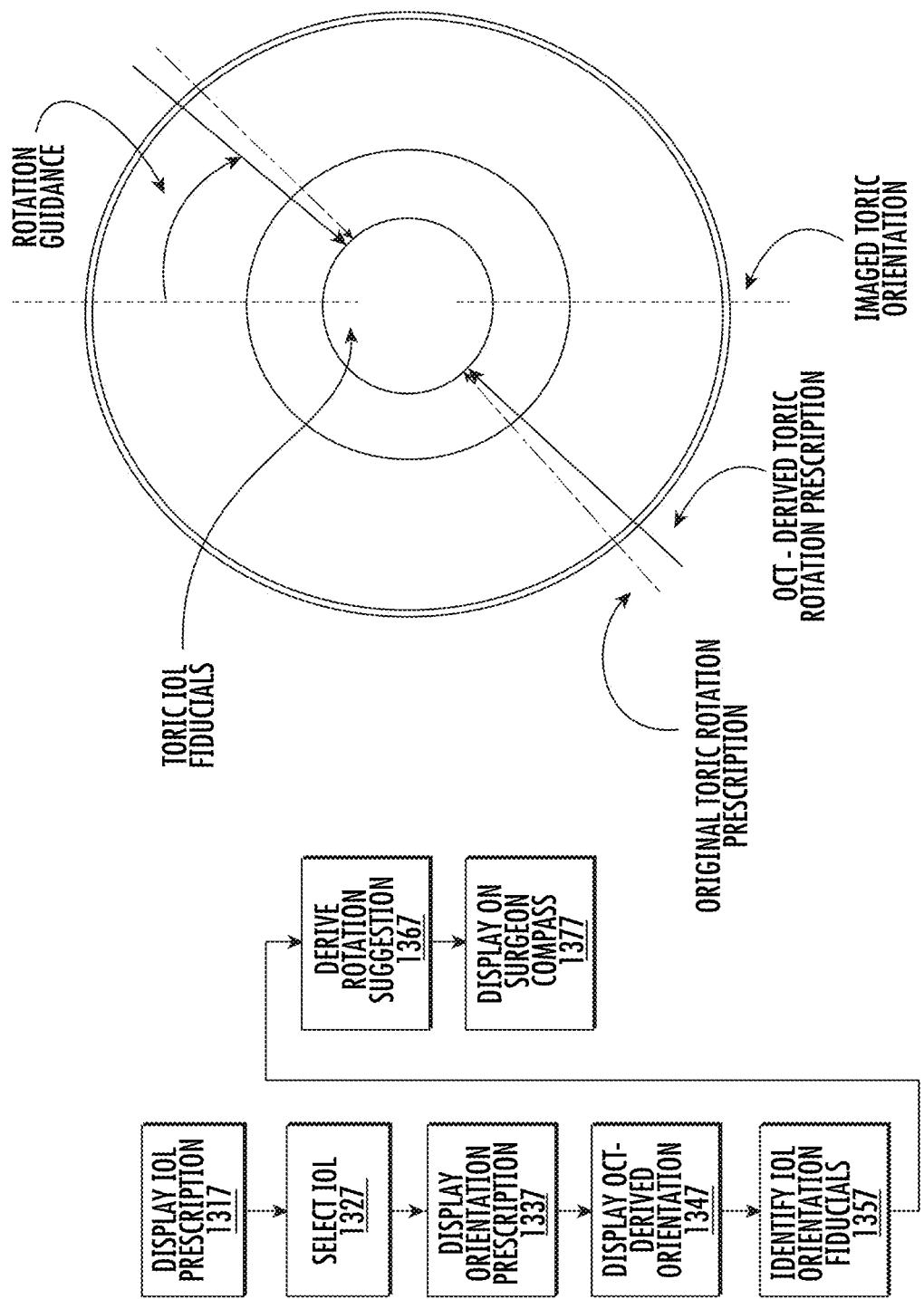
FIGS. 13A and 13B are a flow chart and a diagram, respectively, illustrating operations in guiding IOL placement in accordance with embodiments of the present inventive concept.

A process for identifying epithelial cells in accordance with some embodiments of the present inventive concept will now be discussed with respect to the flow chart of FIG. 12. Operations begin at block 1216 by obtaining a high density scan of the posterior capsule, full sampling the posterior capsule at a sampling density that is substantially at the lateral optical resolution. The acquired high density volume (scan) may be directly scanned by the surgeon.

Image processing techniques may be applied to the high density volume to highlight any residual epithelial cells. In some embodiments, image segmentation techniques may be used on the posterior capsule (block 1226) to identify the anterior surface of the posterior capsule (block 1236), create a surface that represents this structure, and identify structures that are visible within a window that lies above, or anterior to, this surface, particularly in the immediate vicinity. A particularly useful representation to flatten the data volume to the capsular surface, and create an en face projection of the image that resides above this surface. The en face projection may be derived from a depth slab as thin as a single pixel, or may be averaged over two or more pixels in depth. The en face projection, which may be referred to herein as "a contoured C-slice," may be scanned with software over a region of depth in order to identify residual epithelial cells (debris) as a function of distance off of the capsular bag (block 1246). An exemplary representation of this en face presentation including the residual epithelial cells (or debri), observed in an OCT cross-sectional image, FIG. 16D, is illustrated in, for example, the cellular debris map presented inside the graphical pupil of the eye in FIG. 16E. With this information, the surgeon is well equipped to clear out remaining epithelial cells (debris) to the surgeon's satisfaction, thus reducing the risk of PCO.

Referring again to FIG. 7, operations proceed with orienting the IOL (block 771). An astigmatism-correcting toric IOL should be rotationally aligned in order to provide the desired correction. Errors in alignment of even one degree may lead to measurable errors in refraction. As illustrated in FIG. 13B, toric IOLS have radial fiducials 1318 embedded on the lens. A fiducial marker or fiducial is an object placed in the field of view of an imaging system which appears in the image produced, for use as a point of reference or a measure. It may be either something placed into or on the imaging subject, or a mark or set of marks in the reticle of an optical instrument. Conventional methods for placing toric IOLS begin with manually marking the proper rotational placement using a surgical ink on the white of the eye. Manually marking is inherently inaccurate. Furthermore, the ink has a tendency to bleed when applied to the white of the eye and, therefore, increases the marking accuracy.

Referring now to FIGS. 13A and 13B, OCT-guided orientation (or marking) will be discussed. OCT guided orientation may provide a better way of marking than manually marking and may lead to fewer errors and, thus, may be an important improvement. Referring to FIGS. 13A and 13B, in OCT-guided toric alignment, the IOL prescription is displayed on the surgeon's compass (block 1317), the IOL is selected (block 1327) and imaged. The orientation prescription is displayed (block 1337) as well as the OCT-derived orientation (block 1347) on the surgeon's compass. The fiducials 1318 are identified automatically (block 1357) as illustrated in FIG. 13B. Rotation suggestions are derived (block 1367) and displayed, for example, on the surgeon's compass with guidance provided to the surgeon for re-orientation (block 1377).

In some embodiments, the prescription may be re-tested directly with OCT imaging metrology, and, unlike other techniques such as in situ aberrometry, contributions to refraction can be identified by layer or structure. Post-phaco, it is desirable to retest the prescription. However, ocular pressure changes due to fluid in-flow and out-flow during the procedure. Aberrometry is impacted by the change in pressure. OCT may be used to monitor pressure and provide guidance to the surgeon as will be discussed with respect to the flow chart of FIG. 14.

Figure 14:
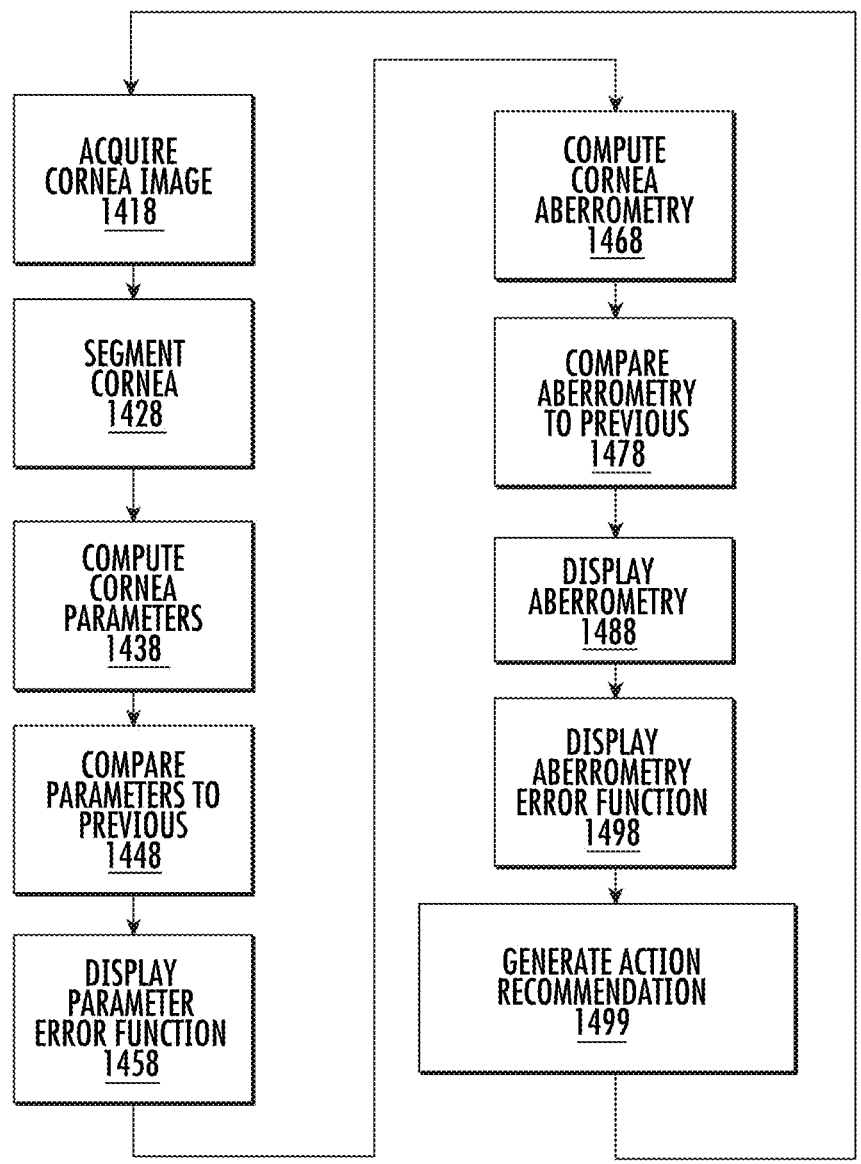
FIG. 14 is a flow chart illustrating operations in managing Intraocular pressure (IOP) in accordance with embodiments of the present inventive concept.

As illustrated in FIG. 14, operations begin at block 1418 by acquiring a cornea image. Anterior and posterior boundary layers are segmented using image processing techniques (block 1428). Topographic and tomographic parameters are computed (block 1438), which may include anterior and posterior curvatures and thicknesses. A useful approach is to generate anterior and posterior surface curves, and compare the surfaces during the procedure to surfaces acquired pre-procedure (block 1448). An error function is displayed (block 1458), either in three-dimensional graphic or wireframe, or on a two-dimensional projection, for example on the surgeon's compass view. In some embodiments, the error function may be color coded for radius of curvature, with a reduced radius of curvature signifying loss of pressure and an increased radius of curvature indicating increased pressure. The structural information may be supplemented with aberration information (block 1468), again comparing intra-surgical values with original values (block 1478). The aberrometry may be displayed (block 1488) and an error function may be calculated (block 1498). The surgeon may then fill or bleed the eye accordingly based on a recommendation (block 1499). Because the hydration state of the cornea may change during surgery, both anterior and posterior surfaces, along with thickness and aberrations are useful, so that the surgeon can apply appropriate judgment to any modification of the surgical plan. As a rapid surrogate, the posterior surface curvature may provide the most direct information on ocular pressure.

Figure 15:
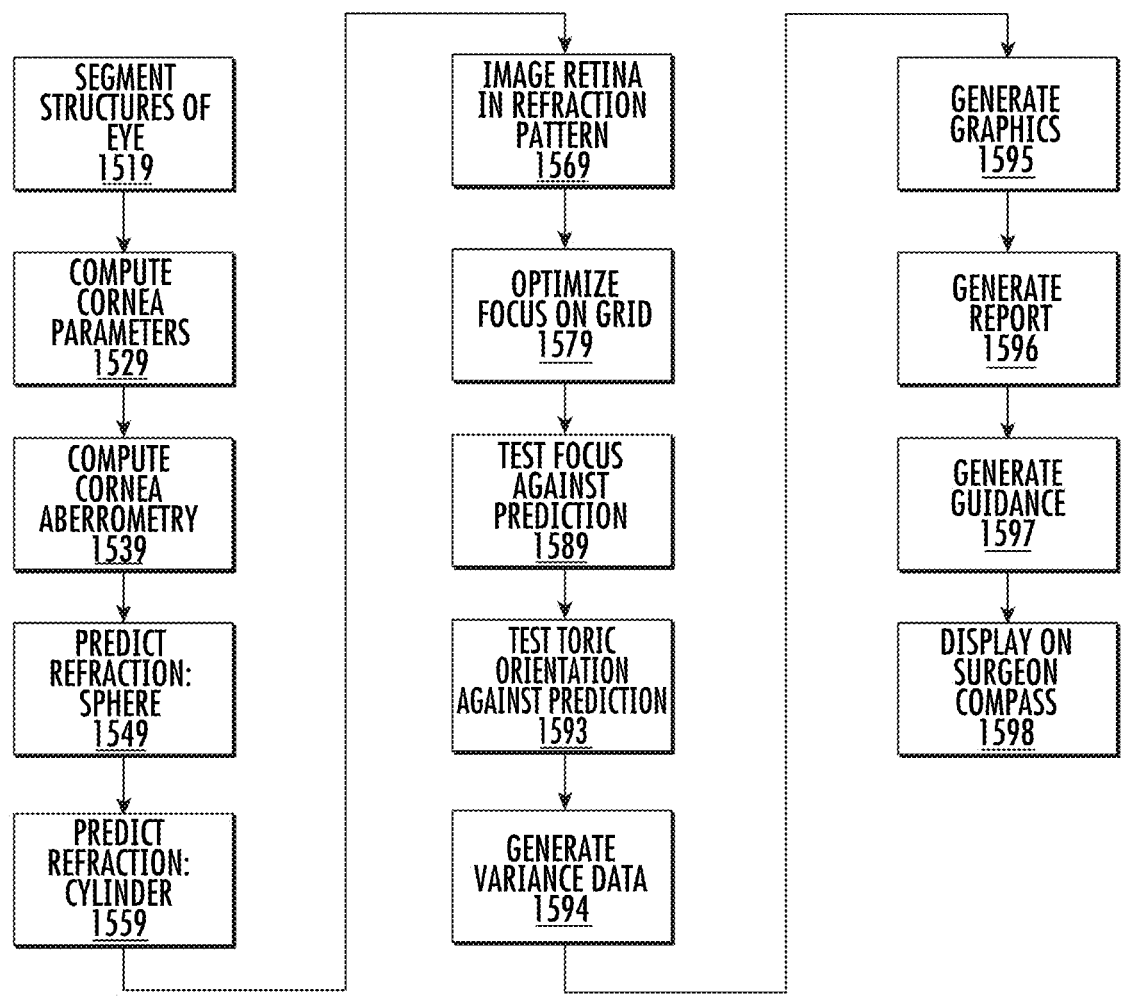
FIG. 15 is a flow chart illustrating operations in retesting IOL prescription in accordance with embodiments of the present inventive concept.
Figure 16:
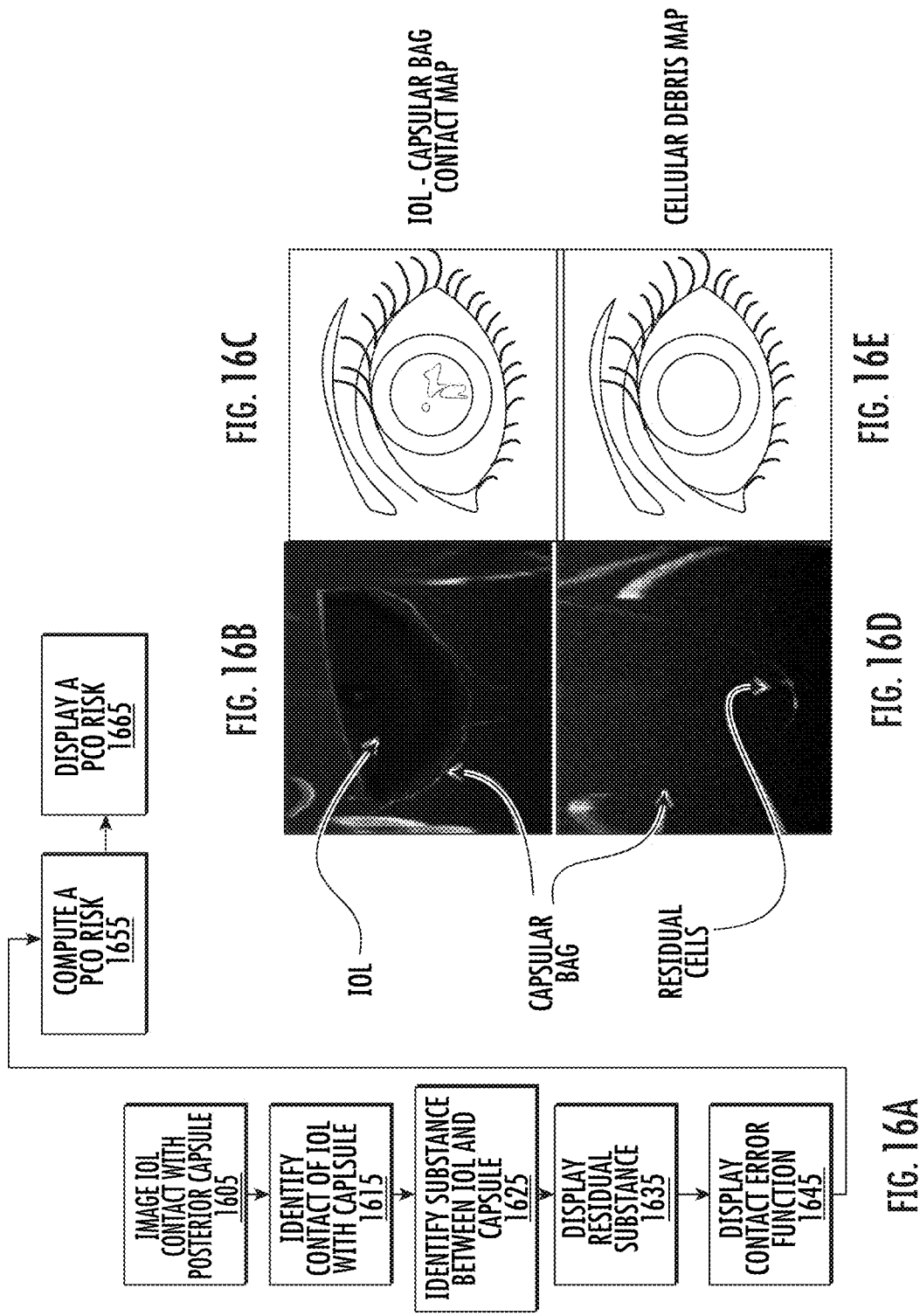
FIGS. 16A and 16B-E are a flow chart and diagrams, respectively, illustrating operations in assessing posterior capsular opacification risk in accordance with embodiments of the present inventive concept.

With the eye at the target pressure, the clinical parameters of interest may be recomputed either before or after IOL placement as will be discussed with respect to the flow chart of FIG. 15. Operations begin at block 1519 by segmenting structures of the eye. Cornea parameters (block 1529) and aberrometry (block 1539) may be computed. A prediction may be about the refraction sphere (block 1549) and cylinder (block 1559). The retina may be imaged in a refraction pattern (block 1569) and focus may be optimized on the grid (block 1579). The focus and toric orientation may be tested against the prediction (blocks 1589 and 1593). Variance data may be generated (block 1594). Graphics, reports and guidance may be generated (block 1595-1597). The results may be displayed on the surgeon's compass (block 1598).

Thus, with the cataract cleared, it may become possible to image the retina, for the first time or with greater than pre-surgery. In addition, the steps of computing topography, thickness and aberrometry to derive refraction and astigmatism, the refraction can be tested directly by testing optimum focus while imaging the retina directly, as discussed above. Testing the optimum OCT focus on the retina provides a strong functional confirmation of the computations and validates the performance of the surgery. An error function of the focus adjustments against computational predictions, and prescriptive predictions can be presented to the surgeon for further correction if required.

Referring again to FIG. 7, refraction may be assessed (block 781). In addition to achieving correct refraction, it is important to relieve epithelial cells from the region directly posterior to the IOL and within the line of vision. Referring now to the flow chart of FIG. 16A, as it is possible that peripheral epithelial cells may remain, a risk-reducing surgical approach (block 791) is to position the IOL such that full circumferential contact is made between the edge of the IOL and the capsule (block 1605). This contact is difficult to judge through the surgical microscope. The OCT image acquisition and display technique discussed above may also be used to evaluate the degree of contact of the IOL with the capsule, and to display an error function in an en face projection to identify regions of poor contact.

In particular, as illustrated in FIG. 16B, the OCT system may identify contact of IOL with the capsule (block 1615) and any substance (residual cells—FIG. 16C) between the IOL and the capsule (block 1625). As illustrated in FIG. 16E, the residual substance may be displayed (block 1635). The contact error function may be displayed in an en face projection to identify regions of poor contact (block 1645). Finally, a PCO risk and may be computed (block 1655) and displayed (block 1665). Removing posterior epithelial cells and assuring circumferential contact between the IOL and the capsule may reduce the risk of PCO.

Figure 17:
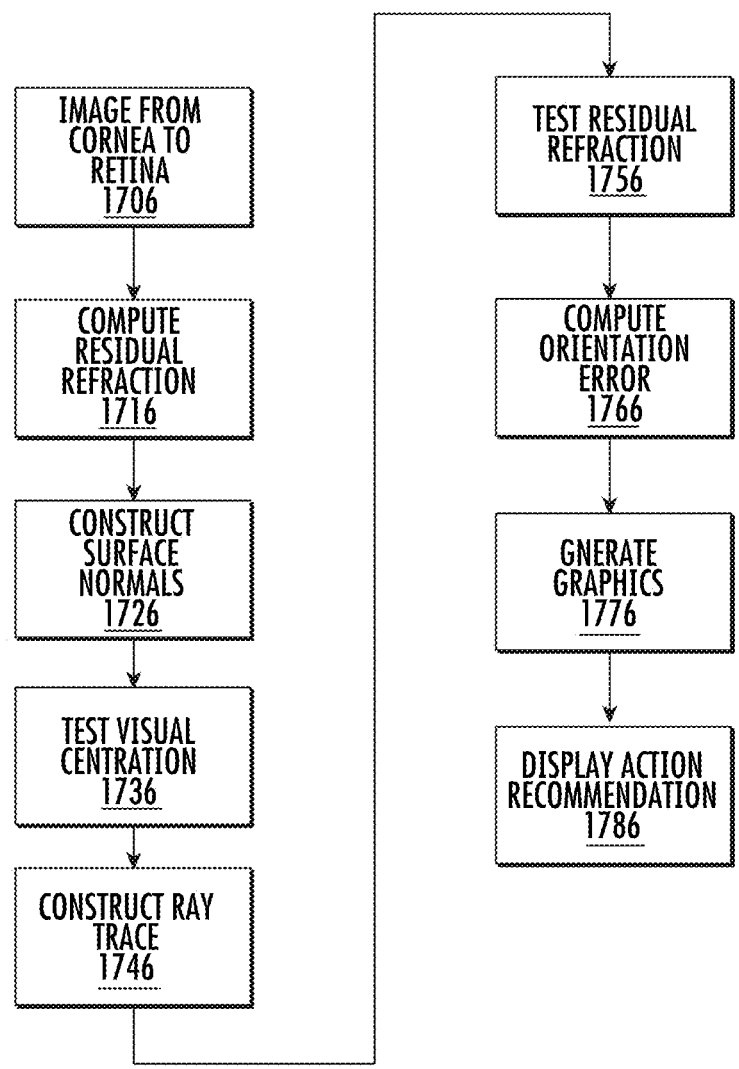
FIG. 17 is a flow chart illustrating operations for confirming IOL and alignment in accordance with embodiments of the present inventive concept.

With the IOL in place, additional corrections may be made with the help of OCT visualization which are not generally possible otherwise. For example, FIG. 17 is a flow chart illustrating operations for confirming IOL and alignment in accordance with embodiments of the present inventive concept. The eye may be imaged from the cornea to the retina (block 1706). Residual refraction may be computed (block 1716) and surface normals constructed (block 1726). Visual centration may be tested (block 1726) and a ray trace may be constructed (block 1746). The residual refraction may be tested (block 1756) and an orientation error is computed (block 1766). Graphics are generated (block 1776) and a recommendation will be made (block 1786).

Two other alignment attributes are important and not readily addressed otherwise: angular alignment and centration to the visual line of site. Total alignment is readily assessed with this OCT imaging technique. Angular alignment may be directly assessed with a multi-slice or volumetric acquisition of the IOL in situ. The angular alignment may be visualized qualitatively with the display of cross-sections, a three-dimensional volume view, or a wire-frame construction. Additionally, a surface profile may be derived by segmenting the anterior and/or posterior surfaces of the IOL, and normal vectors constructed. The normal vector may be resolved into nasal-temporal and inferior-superior directional components. The vector may be displayed in a 3D-type view, or the projections of the vector may be displayed on the surgeon compass. As the surgeon improves the angular alignment, the vectoral display may be updated, and a visual or audible signal offered to provide feedback to the surgeon.

The centration with respect to the line of site may also be readily assessed. A stack of images may be obtained of the cornea, lens, and retina without any change in position of the microscope with respect to the patient, by controlling the focus and reference arm as discussed above. With these image sectors, the alignment may be immediately visualized. A cornea apex, IOL apex, and macula may be identified using the image processing techniques discussed, and normal vectors to these positions computed. The centration features may be plotted on the surgeon's compass view. The normal vectors may be plotted in multiple ways, including plotting individual projections on the surgeon compass, as discussed above, plotting difference vectors in a similar manner, or drawing 3D vectors in space to highlight the agreement or disagreement in optical lines of site. The surgeon may determine appropriate corrective action based on this information, or a set of clinical limits may be established to provide more direct instruction to the surgeon.

Figure 18:
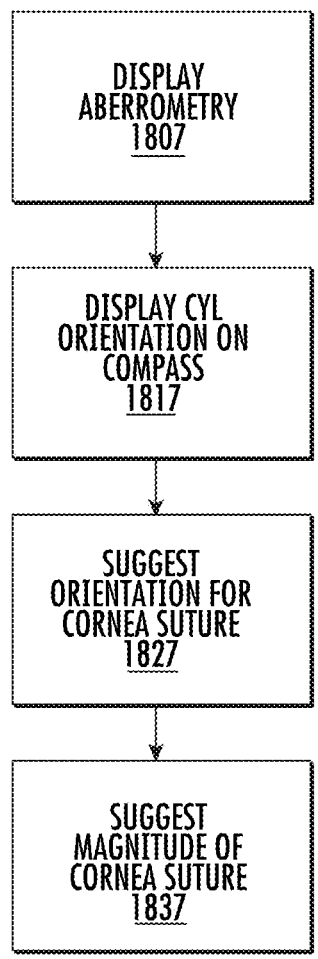
FIG. 18 is a flow chart illustrating operations for tuning residual astigmatism in accordance with embodiments of the present inventive concept.

As a final stage in the procedure, the surgeon may choose to make a final correction to tune the results, as illustrated in FIG. 18. The OCT may be used as previously described to obtain a final set of clinical outputs, including refraction and astigmatism. It is well known that cornea suturing impacts astigmatism, and strategic suturing may be used to induce a corrective astigmatism. In particular, the aberrometry may be displayed (block 1807) and the orientation may be displayed on the surgeon's compass (block 1817). Based on the OCT analysis, a proposal for location of a corrective suture may be proposed, and highlighted on the surgeon's compass (block 1827). Additionally, the compass view may provide a scale to indicate the severity of the astigmatism, to guide the surgeon on the strength of the correction required (block 1837).

Figure 19:
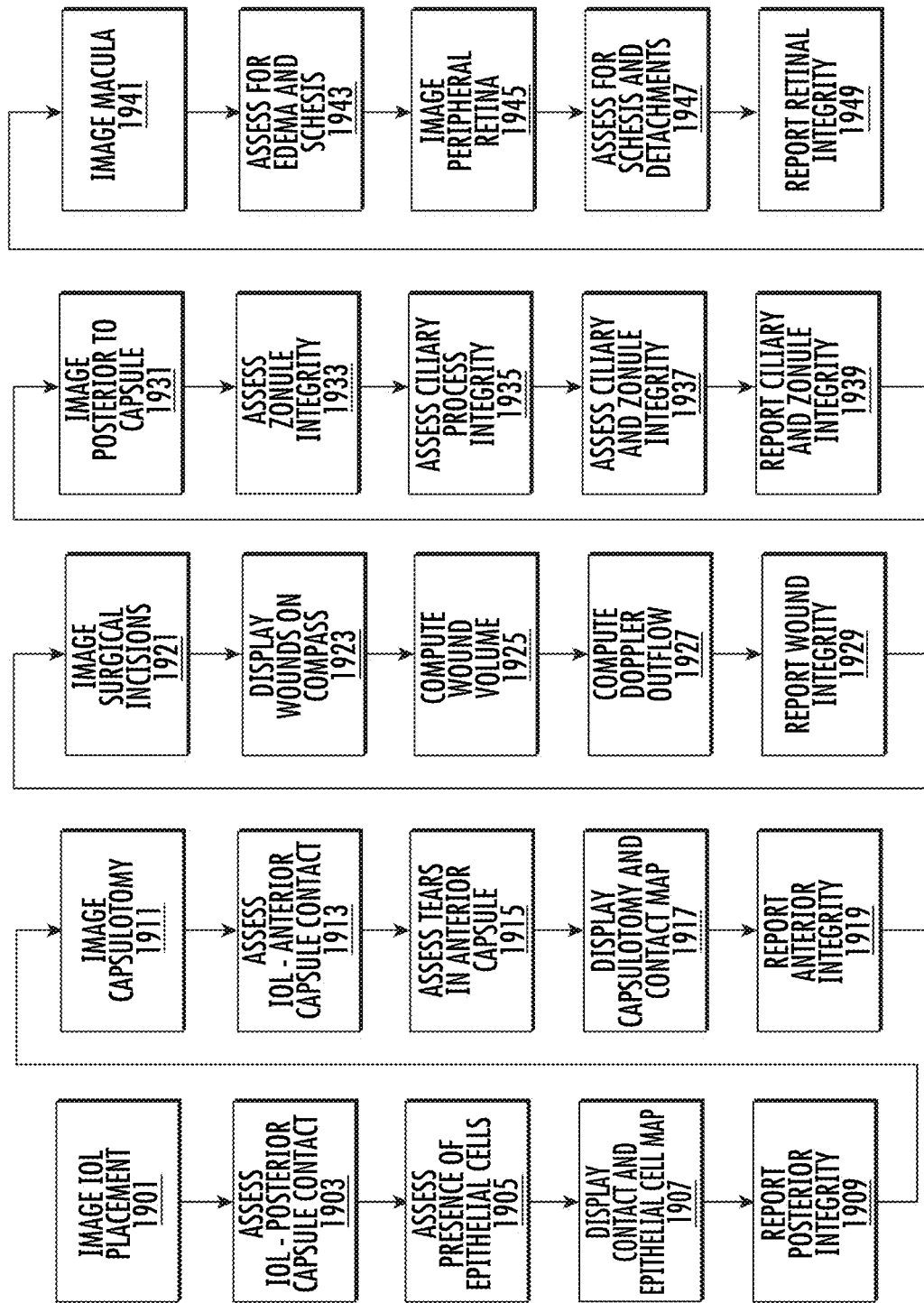
FIG. 19 is a flow chart illustrating operations for assessing post-procedure integrity in accordance with embodiments of the present inventive concept.

At the completion of the surgery (FIG. 7—block 795), OCT may be used to assess the structural outcome and identify any potential risks that may be visualized in order to allow correction during a single procedure. As illustrated in FIG. 19, the IOL placement may be visualized and impact computed as discussed above. The capsular integrity may be assessed tears identified, or any non-uniformities in positioning of the IOL with respect to the capsule highlighted (block 1901-1919). As wound healing is an indicator of endophthalmitis, the limbal incisions may be imaged (block 1921), leakage identified, and excess damage to the wound identified (block 1923-1929). If necessary, the surgeon may choose to suture or allow self-sealing or otherwise. OCT-based Doppler imaging may be used to directly image fluid outflow. The OCT may be used to image the zonules (block 1931-1933), supporting structures to the capsular bag, and the ciliary process, to identify damage or stress that might lead to lens displacement, or stress to the retina that creates risk of retinal detachment or schesis (block 1935-1939). The macula itself may be imaged (block 1941) for edema, schesis, or detachment (blocks 1943-1949). These images may be acquired without a lens change, by using the focal control and reference arm control discussed above.

Figure 20:
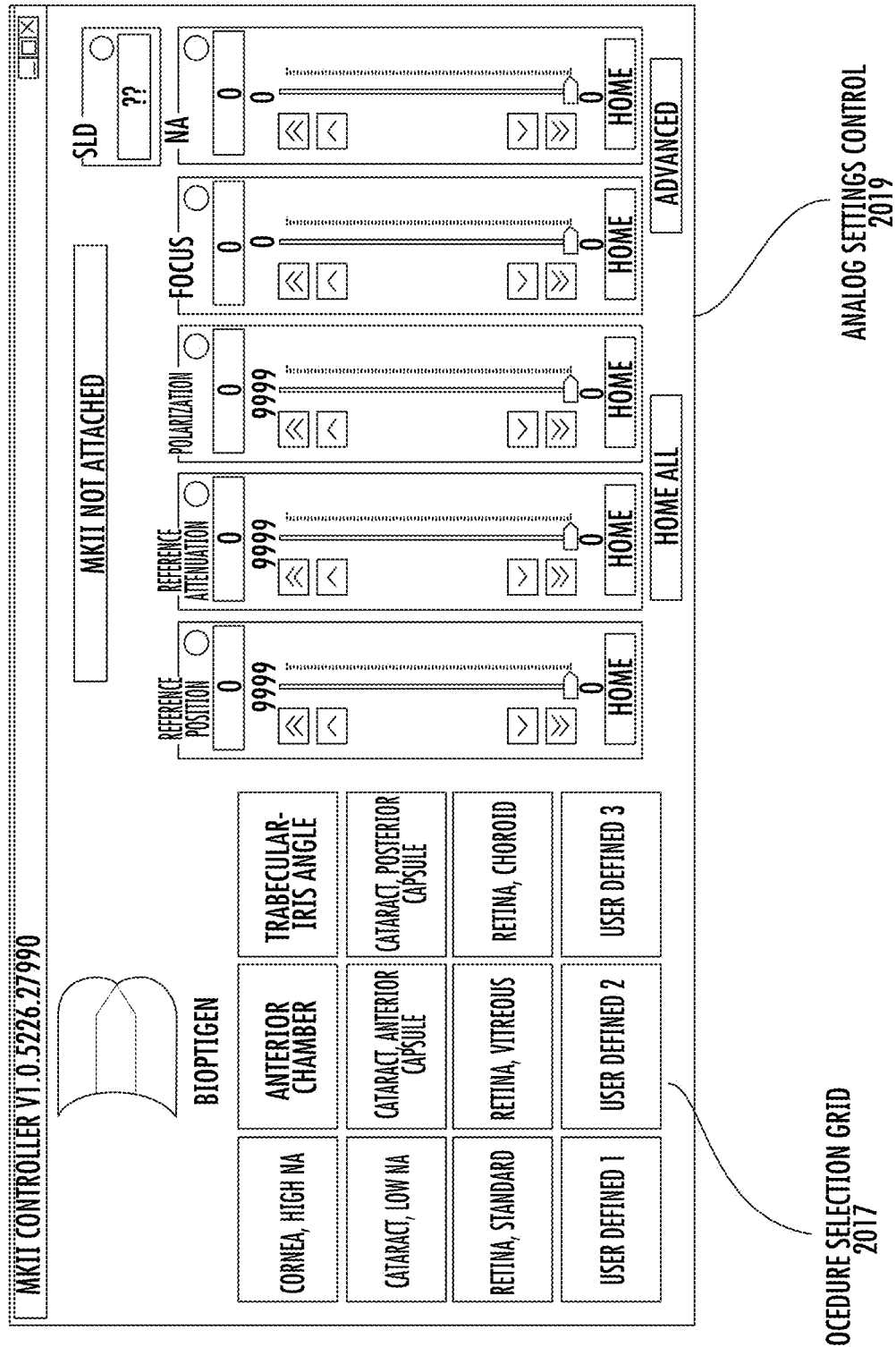
FIG. 20 is a screen shot illustrating a software interface designed to facilitate configuring an optical coherence tomography imaging system in accordance with some embodiments of the present inventive concept.

A software interface designed to facilitate configuring an optical coherence tomography imaging system for acquiring optimal images is dependent on the region to be imaged or interventional procedure to be performed according to some embodiments is shown in FIG. 20. It will be understood that embodiments of the present inventive concept are not limited to the interface of FIG. 20 and that FIG. 20 is provided as an example only.

An OCT imaging system typically has a number of physical settings and software processing parameters that are set for an imaging session. These parameters, for convenience, may be categorized as scan parameters, engine or interference parameters, signal processing parameters, and display parameters. Scan parameters may include a scan pattern, a scan range, and a scan sampling density, a beam focus, and a beam numerical aperture. Other parameters may include an averaging parameter, a synchronization or other timing parameter, among others. Engine or interferometer parameters may include settings to control the power of a light source, the coupling ratio of a beamsplitter, the reference path length, the attenuation level of the reference path, and the polarization setting of the reference path, among others. Additionally, the engine or interference parameters may include detection control parameters, including but not limited to, detector integration times. Signal processing parameters may include parameters related to transforming the spectral data from the interferometer to spatial data. These parameters may include numerical dispersion compensation coefficients, and may also include other apodization parameters applied to a Fourier transform. Other parameters may also be used in the mathematical transformation process according to some embodiments. Display parameters may include parameters related to noise reduction, the range of data displayed on a screen, and brightness and contrast parameters. The options for display parameters may be readily extended to meet the user requirements.

Because the parameter space for optimizing an image for a variety of circumstances may be quite expansive, as described above, it may not be efficient for the operator to search the parameter space for an optimum image at each step in an interventional process. FIG. 20 illustrates a useful and efficient solution to rapid system setting. On the left side of FIG. 20, a procedure selection grid 2017 is diagrammed with a series of control buttons. Each button describes a unique imaging circumstance, the individual buttons and the set of buttons being defined for the particular use case or use cases of interest. Each button is named for a procedure or a region of interest. The selection of the button then sends the system request to set the system parameters pre-defined to the particular circumstance. The settings may control one or more specific parameters from one or more of the categories of parameters as described above.

The target parameters appropriately calibrated may be all that is needed to set the OCT system for optimum or acceptable image acquisition and display. However, there may be circumstances where additional fine tuning is required. A software user interface that includes analog controls of the key parameters may be desired. Thus, analog settings controls are also illustrated in FIG. 20. In the display example of FIG. 20, reference arm position, reference arm attenuation level, and polarization balance are shown, as well as focus and numerical aperture control of the scanning beam. However, it will be understood that embodiments of the present inventive concept are not limited to this configuration.

In some embodiments of the present inventive concept, the procedure or region of interest is selected, and the system set up is accomplished by the system controller after the user selects the appropriate control on the user interface. The analog controls are set to reflect the current system configuration, and provide a range and granularity of control useful for fine tuning of the imaging given the control selection. The user may then use or not use the analog controls as required to obtain an image of the desired quality.

The techniques discussed herein emphasize the utility of procedural optical coherence tomography imaging in cataract surgeries. Many of the same techniques for focusing on a procedural region of interest, acquiring images, segmenting, computing clinically relevant results, and deriving a feed signal, number, or image for the surgeon, are directly applicable to other surgically oriented activities. In ophthalmology, cornea refractive surgery, cornea transplant surgery, and other refractive-modifying procedures will benefit directly from these methods. Retinal surgery will benefit from including refractive information to understand the role of edema and atrophy on total visual outcomes. Glaucoma surgery will benefit from the visualizing and measuring the sclera, the iridocorneal angle, the location of ducts that mediate flow and pressure control between anterior and posterior chambers of the eye. Each of these procedures will benefit from tomographic visualization and measurements that guide in the placement and alignment of implants relevant to the specific therapeutic objective. Outside of ophthalmology, the general method may be useful in areas such as neurosurgery, where depth resolved structural information is important to clinical outcomes, even though the specifics of refractive response and vision may not correctly define the clinically relevant computations.

Figure 21:
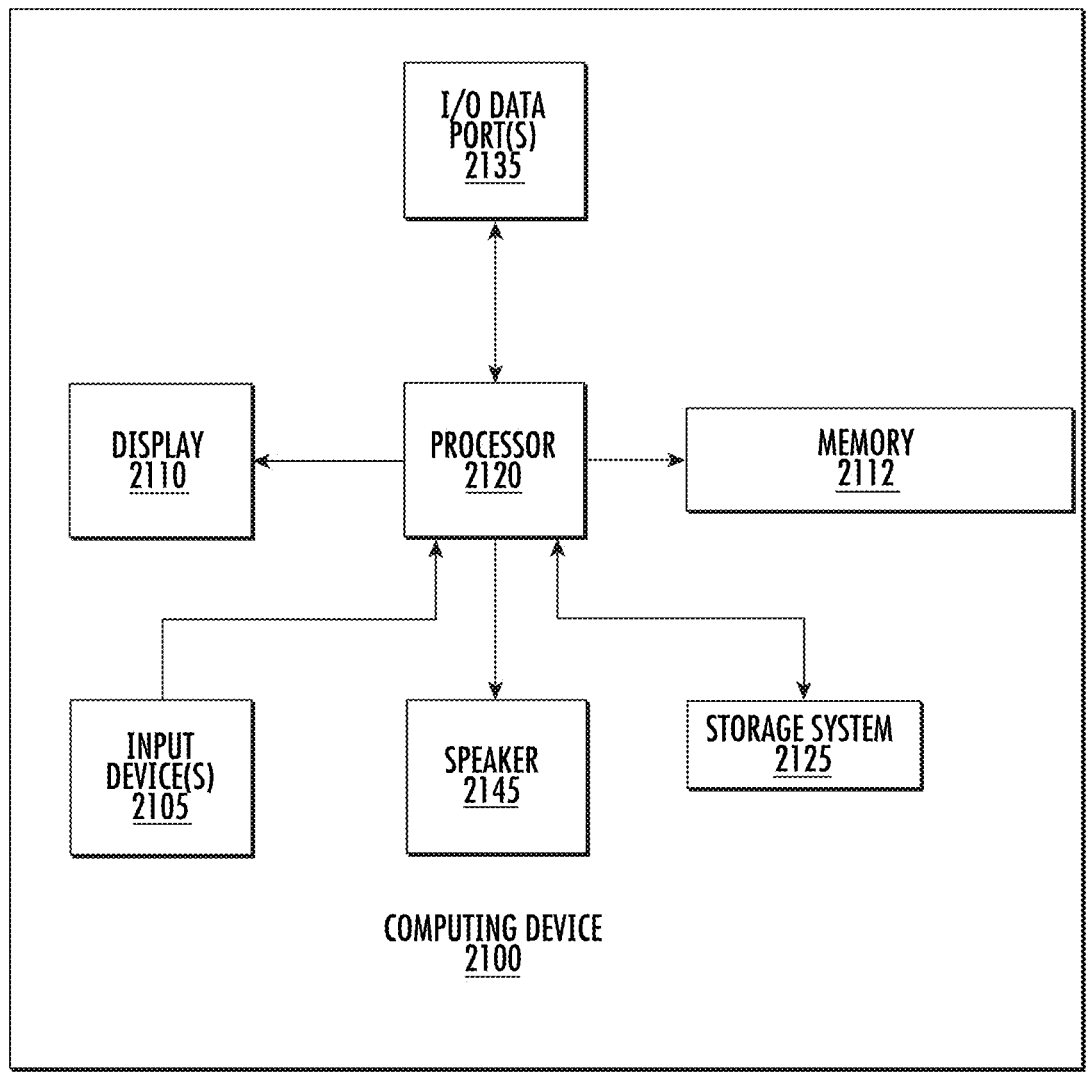
FIG. 21 is a block diagram that illustrates a computing device for use in some embodiments of the present inventive concept.

As is clear from the discussion of embodiments of the present inventive concept above, many of the methods discussed herein require processing provided by a computing device. Referring now to FIG. 21, a block diagram of a general computing device 2100 that can be used to provide the necessary processing in accordance with some embodiments of the present inventive concept will be discussed. The device 2100 may be used, for example, to implement the necessary calculations discussed with respect to the flow charts and diagrams above using hardware, software implemented with hardware, firmware, tangible computer-readable storage media having instructions stored thereon, or a combination thereof, and may be implemented in one or more computer systems or other processing systems. The computing device 2100 may also be a virtualized instance of a computer. As such, the devices and methods described herein may be embodied in any combination of hardware and software.

As shown in FIG. 21, the computing device 2100 may include input device(s) 2105, such as a keyboard or keypad or touchscreen, a display 2110, and a memory 2115 that communicate with one or more processors 2120 (generally referred to herein as "a processor"). The computing device 2100 may further include a storage system 2125, a speaker 2145, and I/O data port(s) 2135 that also communicate with the processor 2120. The memory 2112 may include the OCT data in accordance with embodiments discussed herein as well as other data necessary to provide the necessary information installed thereon.

The storage system 2125 may include removable and/or fixed non-volatile memory devices (such as but not limited to a hard disk drive, flash memory, and/or like devices that may store computer program instructions and data on computer-readable media), volatile memory devices (such as but not limited to random access memory), as well as virtual storage (such as but not limited to a RAM disk). The storage system 2125 may include information used to perform various aspects of the present inventive concept. For example, the storage system may include the OCT system data discussed above. Although illustrated in separate blocks, the memory 2112 and the storage system 2125 may be implemented by a same storage medium in some embodiments. The input/output (I/O) data port(s) 2135 may include a communication interface and may be used to transfer information in the form of signals between the computing device 2100 and another computer system or a network (e.g., the Internet). The communication interface may include a modem, a network interface (such as an Ethernet card), a communications port, a PCMCIA slot and card, or the like. These components may be conventional components, such as those used in many conventional computing devices, and their functionality, with respect to conventional operations, is generally known to those skilled in the art. Communication infrastructure between the components of FIG. 21 may include one or more device interconnection buses such as Ethernet, Peripheral Component Interconnect (PCI), and the like.

The flowchart and block diagrams in the Figures illustrate the architecture, functionality, and operation of possible implementations of systems, methods and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

That which is claimed is:

1. A method for prescribing inter-ocular lens (IOL) orientation using an optical coherence tomography (OCT) imaging system, the method comprising:
    computing, with a processor, target refraction from acquired OCT data provided by the OCT imaging system, refraction including at least one of sphere, cylinder and toric orientation;
    displaying the OCT computed target refraction and orientation on a graphical display for a surgeon performing a surgical procedure;
    comparing the computed target refraction to an original prescription on the graphical display to provide a comparison result;
    determining a final prescription based on the comparison result presented on the graphical display; and
    modifying a surgical plan in real-time based on the determined final prescription, wherein modifying the surgical plan in real-time comprises:
    obtaining at least one image of a surgical region of a subject oriented for the surgical procedure using the OCT imaging system;
    constructing an initial structural view of the surgical region to be used during the surgical procedure based on the obtained at least one image;
    computing a measure corresponding to intraocular pressure using data derived from measurements of a cornea from the obtained at least one image;
    periodically assessing the surgical procedure during the surgical procedure and monitoring clinical outcomes related to the surgical procedure using one of changes to an OCT-derived initial structural view of the surgical region and changes to the computed measure corresponding to intraocular pressure derived from measurements of the cornea from the at least one OCT image;
    determining if a surgical plan for the surgical procedure needs modification during the surgical procedure based on at least one of the periodic assessment and monitoring;
    modifying the surgical plan for the surgical procedure during the surgical procedure if it is determined modification is needed; and
    repeatedly assessing and monitoring, determining and modifying during the surgical procedure until it is determined that modification is not needed.

2. The method of claim 1, wherein the graphical display comprises an en face surgeon compass view.

3. The method of claim 1, further comprising generating a report of the surgical procedure.

4. The method of claim 1, wherein repeatedly is followed by:
    before concluding the surgical procedure on the subject, assessing final clinical outcomes of the surgical procedure by testing the measure corresponding to intraocular pressure derived from measurements of the cornea from the at least one OCT image against a target value.

5. The method of claim 1, wherein determining that modification of a surgical plan is needed comprises:
    acquiring at least one OCT image of region including a surgical incision;
    generating and displaying at least one of a structural cross-sectional OCT image, a structural en face image OCT image, and a Doppler OCT image of the region including the surgical incision; and
    assessing a degree of closure of the surgical incision observed in the structural cross section OCT image or the en face OCT image or assessing presence of flow observed by Doppler OCT through the surgical incision.

6. The method of claim 5, wherein assessing a degree of closure of the surgical incision is followed by concluding the surgical procedure if the assessment of the intraocular pressure and the degree of closure of the surgical incision are satisfactory.

7. The method of claim 4, further comprising generating a report for the surgical procedure, wherein the report includes at least one computed clinical parameter derived from at least one OCT image.

8. The method of claim 1, wherein the surgical procedure is cataract surgery or cornea surgery.

9. The method of claim 1, wherein the surgical procedure is a retinal surgery.

10. The method of claim 1, wherein the surgical procedure is a glaucoma surgery.

11. The method of claim 1, further comprising:
obtaining a wide angle view of a portion of an eye of the subject extending nasally from a cornea apex region of the eye including a lacrimal puncta using the OCT imaging system for use in orienting the eye;
identifying an orientationally asymmetric physiological structure visible within the at least one OCT image that confirms the eye under test to be one of a right eye and a left eye;
creating a graphical display representative of an imaged portion of the eye of the subject using data derived from the at least one OCT image; and
displaying the graphical display to a surgeon performing the surgical procedure, wherein the graphical display includes at least a graphical element that orients the surgeon performing the surgical procedure to the orientation of the eye.

12. The method of claim 1, wherein constructing the initial structural view of the surgical region includes creating a structural map of the subject, wherein creating the structural map comprises:
acquiring a plurality of OCT images across the eye of the subject;
applying segmentation algorithms to the acquired OCT images to differentiate boundaries of structures of the eye identified in the plurality of OCT images; and
computing clinical parameters associated with structure of the eye.

13. The method of claim 1, further comprising performing a capsulotomy, wherein performing a capsulotomy using OCT comprises:
acquiring an OCT image of a lens of an eye;
displaying a target size, shape and position and a current shape of the capsulotomy on a graphical display derived from the acquire OCT image; and
displaying an error function on the graphical display based on the target and the current shape of the capsulotomy to provide guidance to a surgeon performing the surgical procedure.

14. The method of claim 8, further comprising performing phaco fragmentation, wherein phaco fragmentation comprises acquiring a plurality of OCT images of the eye intermittently or continuously allowing a surgeon performing the surgical procedure to evaluate risks and abnormalities during the procedure.

15. The method of claim 11, further comprising managing Intraocular pressure (TOP) using OCT, whereby managing intraocular pressure comprises comparing a pre-surgical shape of a cornea to an intrasurgical or post-surgical shape of a cornea.

16. The method of claim 1, wherein the OCT imaging system is a telecentric scanning system having a wide field of view (FOV).

17. The method of claim 16, wherein the telecentric scanning system maintains constant pointing of a scanning beam parallel to an optical axis across the FOV.

* * * * *

UNITED STATES PATENT AND TRADEMARK OFFICE
CERTIFICATE OF CORRECTION

PATENT NO. : 11,622,681 B2  
APPLICATION NO. : 16/665106  
DATED : April 11, 2023  
INVENTOR(S) : Buckland et al.

Page 1 of 1

It is certified that error appears in the above-identified patent and that said Letters Patent is hereby corrected as shown below:

On the Title Page

Foreign Patents, page 2: Please correct "CN 102696125 A 07/2012" to read -- CN 102596125 A 07/2012 --

Signed and Sealed this  
Eleventh Day of July, 2023

Katherine Kelly Vidal  
*Director of the United States Patent and Trademark Office*